(12) United States Patent
White

(10) Patent No.: US 12,310,599 B2
(45) Date of Patent: May 27, 2025

(54) SURGICAL CUTTING DEVICE

(71) Applicant: ARCH Medical Solutions, Huntingdon Valley, PA (US)

(72) Inventor: Patrick M. White, Lewes, DE (US)

(73) Assignee: ARCH MEDICAL SOLUTIONS, Huntingdon Valley, PA (US)

( * ) Notice: Subject to any disclaimer, the term of this patent is extended or adjusted under 35 U.S.C. 154(b) by 670 days.

(21) Appl. No.: 17/738,457

(22) Filed: May 6, 2022

(65) Prior Publication Data
US 2023/0355248 A1 Nov. 9, 2023

(51) Int. Cl.
*A61B 17/16* (2006.01)

(52) U.S. Cl.
CPC ...... *A61B 17/1615* (2013.01); *A61B 17/1666* (2013.01)

(58) Field of Classification Search
CPC . A61B 17/16; A61B 17/1613; A61B 17/1615; A61B 17/1617; A61B 17/162; A61B 17/1622; A61B 17/1624; A61B 17/1626; A61B 17/1628; A61B 17/1659; A61B 17/1662; A61B 17/1664; A61B 17/1666; A61B 17/1684
See application file for complete search history.

(56) References Cited

U.S. PATENT DOCUMENTS

| | | | | |
|---|---|---|---|---|
| 5,203,653 A | * | 4/1993 | Kudla | A61B 17/1666 606/81 |
| 5,376,092 A | * | 12/1994 | Hein | A61B 17/1666 407/54 |
| 5,658,290 A | * | 8/1997 | Lechot | A61B 17/1666 606/80 |
| 6,764,490 B1 | * | 7/2004 | Szabo | A61B 17/1666 606/81 |
| 7,118,575 B2 | * | 10/2006 | Wolford | A61B 17/1666 606/80 |
| 7,922,721 B2 | * | 4/2011 | Lechot | A61B 17/1666 606/81 |

(Continued)

FOREIGN PATENT DOCUMENTS

ES 2334622 A1 * 3/2010 ......... A61B 17/1615

OTHER PUBLICATIONS

Downloaded on Feb. 21, 2022 at Brian Erlander wrote in 2015 at http://blog.supertoolinc.com/2015/01/21/reaming-with-left-hand-spiral-flutes-vs-right-hand-spiral-flutes-vs-straight-flutes/ (1 page).

*Primary Examiner* — Eric S Gibson
(74) *Attorney, Agent, or Firm* — Roach Brown McCarthy & Gruber, P.C.; Kevin D. McCarthy

(57) ABSTRACT

A reamer that creates blind holes in a bone has a reamer body connected to a reamer shaft. The reamer body has a shell curvature having at least a portion of a hemisphere, a convex curved exterior surface and a concave curved interior surface, extending from an apex to a lower edge. The reamer body is capable of being rotated about a perpendicular axis; and has at least a first and second left-hand spiral reamer blade. Each left-hand spiral blade extends from the lower edge to the apex and contacts each other at the apex. Each blade is positioned near a slot. When the reamer body rotates and contacts a bone or tissue, the left-hand spiral blades cut bone and pushes the cut bone toward the apex of the exterior surface.

19 Claims, 17 Drawing Sheets

(56) References Cited

U.S. PATENT DOCUMENTS

| | | | | |
|---|---|---|---|---|
| 8,435,243 B2* | 5/2013 | White | ................ | A61B 17/1666 606/81 |
| 8,523,867 B2* | 9/2013 | Rauscher | ........... | A61B 17/1684 606/81 |
| 8,709,012 B2* | 4/2014 | Muller | ................ | A61B 17/1666 606/79 |
| 9,011,442 B2* | 4/2015 | Victor | ................ | A61B 17/1668 606/81 |
| 10,016,205 B2* | 7/2018 | Sausen | ............... | A61B 17/1666 |
| 10,660,658 B2* | 5/2020 | Chenaux | ............ | A61B 17/1617 |
| 12,193,685 B2* | 1/2025 | Purdy | .............. | A61B 17/1697 |
| 2015/0025559 A1* | 1/2015 | Kulas | ................ | A61B 17/1615 606/180 |
| 2023/0355248 A1* | 11/2023 | White | ................ | A61B 17/1615 |

* cited by examiner

SURGICAL CUTTING DEVICE

FIELD OF THE INVENTION

The present invention is directed toward a surgical cutting tool that is capable of producing a recess in a solid body tissue like a bone and/or cartilage.

BACKGROUND OF THE INVENTION

Acetabular Reaming Systems and Spiral Flute Configurations

Acetabular reaming systems are well known in hip arthroplasty, to prepare bone tissue for receiving a hemispherical implant. An example of the hemispherical implant is disclosed in U.S. Pat. No. 5,658,290 to one of the present inventors, the entire contents of which are expressly incorporated by reference herein and relied-upon, discloses such a system. Acetabular component implantation necessitates a surgeon to ream the acetabular fossa which is time consuming and devastating. Utilizing currently-used reamers (FIGS. 1A and 1B), the size of the tool must be changed repeatedly, normally 5-20 times within a surgery. In every stage, the size of the reamer is increased up to 1-2 mm. This tiring process takes 15-30 minutes and is associated with some injuries to the soft tissue. Furthermore, the risk of mistakes is considerable. Moreover, acetabular reaming systems are designed to create blind-holes instead of through-holes. One might inquire what is the difference between a blind-hole and a through-hole. To address this inquiry, the Applicant defers to a 2015 article found at blog.supertoolinc.com that explains the difference between blind holes and through-holes. Relevant portions of that 2015 article read as follows:

"Left hand spiral reamers should be selected for through holes. A through hole has an opening on the other end. If you put your eye up to the hole, you would be able to see out of the other side of a through hole. A left hand spiral pushed the chips ahead of the reamer and out the other side of the hole. This reduces the chances of scarring the work-piece and reduces the chance of damaging the reamer by previously cut chips. [Additionally] a left hand spiral helps bridge interruptions such as cross-holes or keyways. Left hand spirals are excellent for reaming hard materials and typically provide the best side and finish as compared to right hand spiral or straight flutes.

Right hand spiral reamers should be selected for blind holes. A blind hole is a hole that does not have an opening on the other end. If you were to put your eye up to the hold, all you would see is darkness. In a sense, you would be "blind" while looking in the hole. A right hand spiral pulls the chips towards the back of the reamer. This helps prevent the chips from getting packed into the bottom of the hole reducing the chance of damaging the reamer and the work piece by previously cut chips. Additionally a right hand spiral also helps bridge interruptions such as cross-holes or keyways. A right hand spiral reamer may cut slightly oversized holes due to the aggressive flute geometry. They perform very well in highly ductile materials."

Based on that information that is deemed conventional wisdom, those skilled in the acetabular reaming system art understand and appreciate that right hand spiral reamers are required to form blind holes. Applicant has created an acetabular reaming system that contradicts that understanding.

Conventional Acetabular Reaming Systems

In the afore-mentioned patent, a surgical driver 1 includes a quick disconnect mechanism 9 having catches 31 that receive at least one orthogonal bar 3, 3', 3" from a domed cutting tool 2, 2', 2". Examples of the orthogonal bars are disclosed in U.S. Pat. No. 10,660,658. In the '658 patent, Chenaux illustrated at FIG. 1A a conventional surgical driver 1 and conventional orthogonal bar 3, 3', and 3" configurations from, respectively, a domed cutting tool 2, 2', 2".

It is highly desirable that the bone is shaped by the rotary tool into a blind-hole cavity that conforms closely to the soon to be received implant's hemispherical shape and dimension. Those skilled in the art have sought to provide rotary cutting tools that form the bone into a precise hemispherical blind-hole cavity. It is further desirable to advance the tool linearly into the bone to fully cut the cavity, versus having to rock the tool sideways by changing its orientation to achieve a complete and desired hemispherical blind-hole cavity shape.

For example, one system has a tool with a cylindrical rim that continues parallel past the hemispherical equator of the tool, in order to allow presentation of teeth for a full cut. Such prior domed tools are referred to as "high-rim" reamers. Although these high-rim reamers have teeth presented for a straight-in (linear) advancement of cut into the cavity, there is no visual confirmation guiding the user to the finished cut. Actual position of the outer equatorial edge of the tool in the bone cavity is obscured and the user does not know exactly when to stop pushing in the tool.

Another type of tool is found in what is known as "hemispherical" reaming systems. These tools have no teeth presented for a full cut of the cavity simply by linear advancement of the tool into the bone. That is, a full, a straight-in cut is not possible hence the tool must be rocked sideways in order to present the teeth for cutting the final shape. This may result in over-cutting the cavity.

Other surgical cutting tools are known. Examples of surgical cutting tools are disclosed in U.S. Pat. Nos. 8,709, 012; 5,376,092; and 5,203,653. In expired U.S. Pat. No. 5,203,653; Kudla claims a reamer for shaping a socket having a cutting head, at least three elongate helical slots, and cutting edges.

The cutting head has a conventional hemispherical shape having a hemispherical exterior surface that defines a hollow chamber.

The three elongate helical slots are always illustrated in U.S. Pat. No. 5,203,653; as being a right-handed flute configuration. That right-handed flute configuration conforms to the conventional acetabular reamer designs for forming a blind hole. Each right-handed helical flute slot configuration extends "along a single plane oriented at a predetermine angle oriented at a predetermined angle between 20° and 50° to the polar axis of said hemispherical portion between said hemispherical exterior surface and the hollow chamber". Also, each right-handed helical flute slot configuration converges toward the center point of the hemispherical exterior surface but being unconnected to each other at the center point.

Each cutting edge in U.S. Pat. No. 5,203,653; is positioned on the trailing portion of each right-handed helical flute slot configuration and raised slightly above the hemispherical exterior surface of the hemispherical portion for moving material from the socket into the hollow chamber during the rotation of the reamer. Kudla describes and illustrates that the cutting edge is positioned (a) only on the trailing edge of the right-handed helical flute slot area and (b) above at least a portion of the slot area's leading edge ("leading edge is below cutting edge") as a result of the leading edge and the trailing edge being cut at a predetermined angle.

Hein, in U.S. Pat. No. 5,376,092; describes a similar reamer 10 product having a substantially hollow hemispherical cutting head 12 (see, FIG. 1B—which is FIG. 2 in the '092 patent) and at least two slots 14. Each slot 14 (a) is a right-hand helical flute that converges near the center point of the hemispherical exterior surface but never converge with another slot, and (b) has (i) a leading edge 18 and (ii) a cutting edge 16 (with optional serrations 24) on the trailing portion. Grooves 66 extend from slots. At least two grooves 66, as described at column 4, lines 40 to 43, "actually traverse the center point." Each of the at least two grooves 66 has a cutting edge 16. Hein expresses that the cutting edge 16 on the at least two grooves "traverse the center of the cutting head 12." That statement is disingenuous since (A) Hein clearly illustrates the cutting edges (identified as 16A and 16B) of the at least two grooves 66, and the at least two grooves are always separated from each other by a narrow groove space 67 that is illustrated and identified at FIG. 1B; (B) cutting edge 16A must face a first direction while cutting edge 16B must face a second direction that is opposite the first direction; (C) it is impossible to have two cutting edges 16A and 16B facing in opposite directions in the narrow groove space 67 without one or the other cutting edge 16A, 16B being damaged expeditiously. Accordingly, Hein illustrates two cutting edges 16A, 16B approaching the center of the cutting head, but remain separated by the narrow groove space 67. Otherwise, a patient's bone or tissue will be damaging Hein's reamer configuration.

It is also well known that reamers that create blind holes in a bone have a bladed cutting head with a right-handed flute configuration grab the bone, tissue, and/or cartilage. Grabbing bone, tissue, and/or cartilage is undesirable and has been recognized by some of the above-identified patents. In particular, some of the above-identified patents attempted to solve that grabbing problem with a depth stop feature. Utilizing a depth stop feature in any reamer having a bladed cutting head with a right-handed flute configuration that creates a blind hole in a bone continues to grab the bone, tissue, and/or cartilage.

The current invention solves this grabbing problem by violating the intuitive knowledge about blind-hole reamers.

SUMMARY OF THE INVENTION

A reamer that creates blind holes in a bone has a reamer body connected to a reamer shaft. The reamer body has a shell curvature having at least a portion of a hemisphere, a convex curved exterior surface and a concave curved interior surface, extending from an apex to a lower edge. The reamer body is capable of being rotated about a perpendicular axis; and has at least a first and second left-hand spiral reamer blade. Each left-hand spiral blade extends from the lower edge to the apex and contacts each other at the apex. Each blade is positioned near a slot. When the reamer body rotates and contacts a bone or tissue, the left-hand spiral blades (a) cut bone or tissue to create cut bone chips or cut tissue chips, and (b) pushes the cut bone chips or the cut tissue chips toward the apex of the convex curved exterior surface, so the cut bone chips or the cut tissue chips break and dislodge free from the bone or the tissue.

DETAILED DESCRIPTION OF THE INVENTION

Figure 1A:
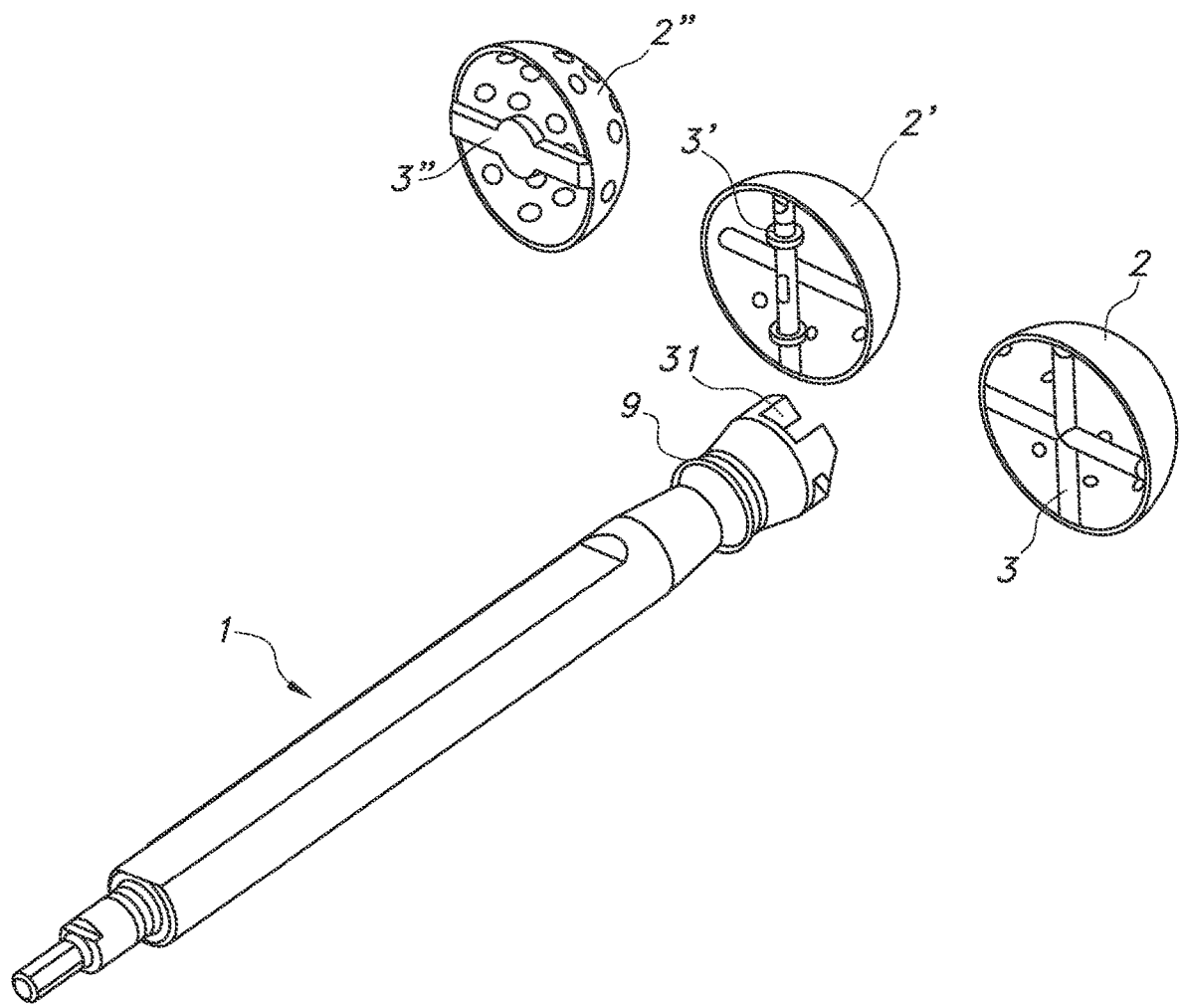
FIGS. 1A and 1B are prior art acetabular reaming tools.
Figure 1B:
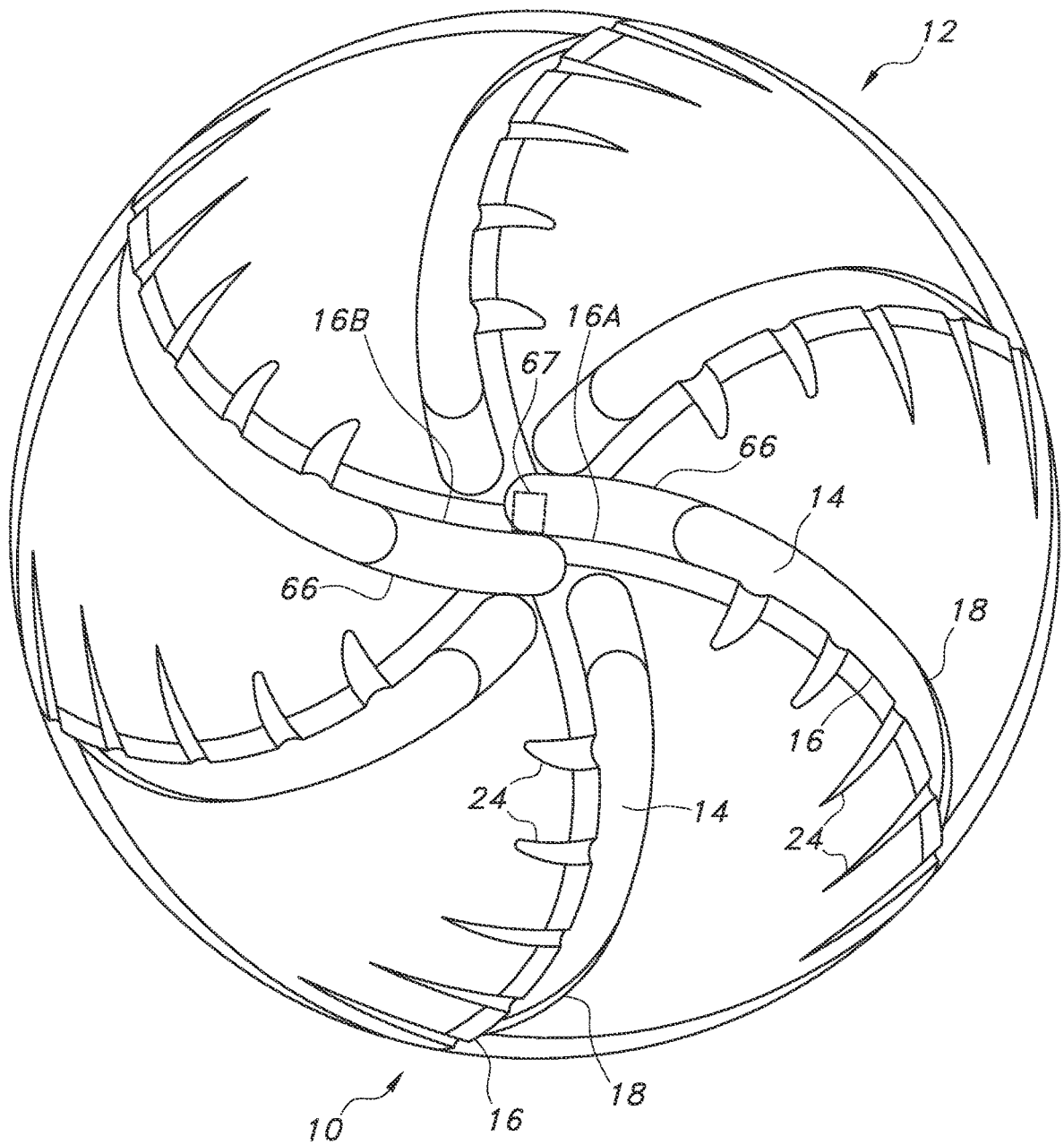
Figure 2:
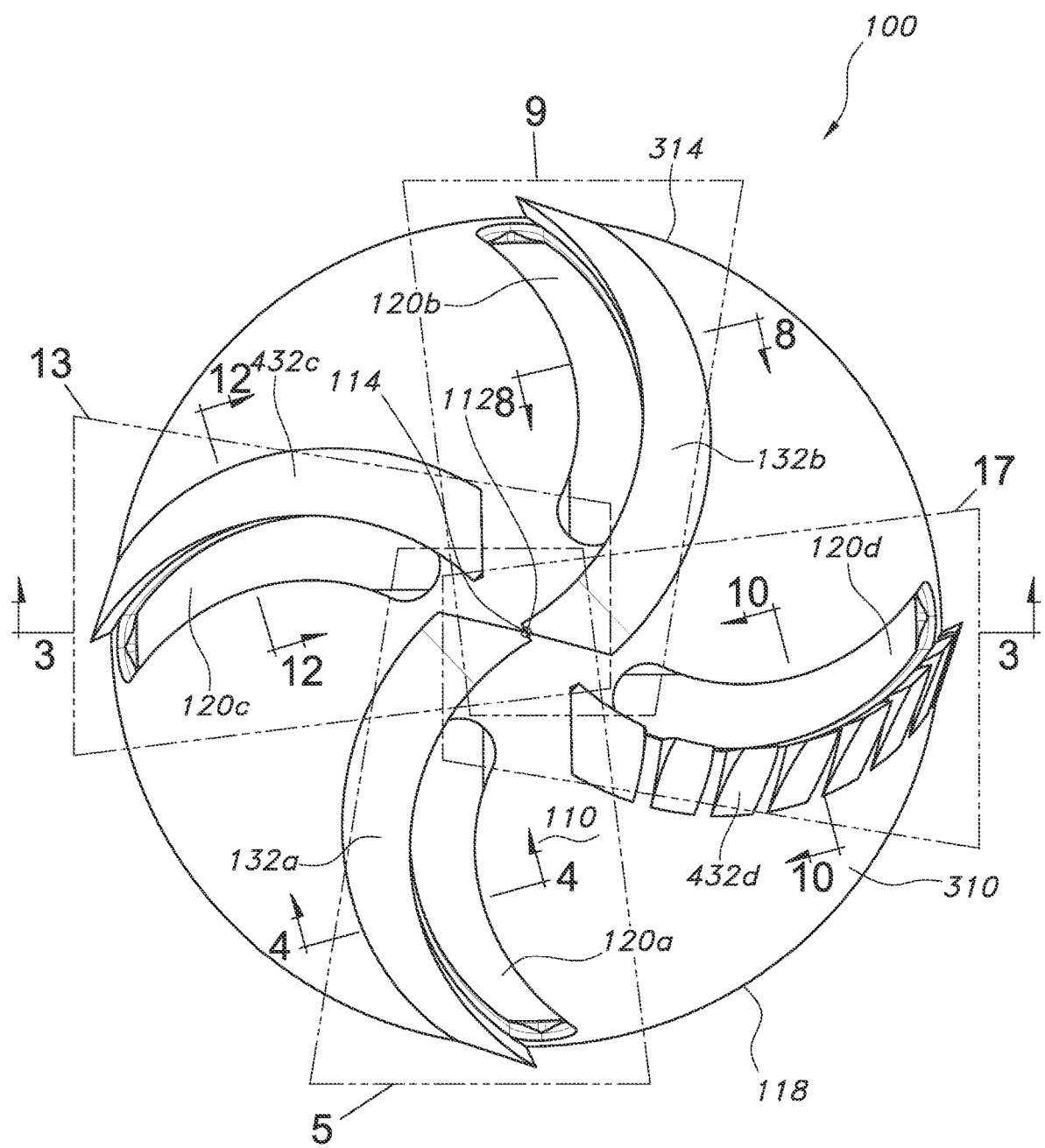
FIG. 2 illustrates the present invention's acetabular reaming tool.

The current invention is directed toward an acetabular reaming tool 100 (see FIG. 2) for shaping a bone socket and in particular, an acetabular socket prior to implantation of a prosthetic acetabulum (not shown). The acetabular reaming tool 100 has a substantially hemispherical and hollow cutting head 110.

The substantially hemispherical and hollow cutting head 110 has a reamer body 310. The reamer body 310 has a shell curvature 314 comprising at least a portion of a hemisphere that has a convex curved exterior surface 316 and a concave curved interior surface 318, extending from an apex 114 to a lower edge 118. The reamer body 310 being rotatable about a perpendicular axis (also called a rotational axis) 112. The reamer body can also have a reamer shaft 312 (see, FIGS. 3a-c) extending from the apex 114 of the concave curved interior surface 318 or a socket 305 (see, FIG. 3d) or a male adapter 307 (see, FIG. 3e) positioned at the apex 114 of the concave curved interior surface 318 so a reamer shaft (not shown) can be connectable to the socket or the male adapter. That way, the reamer 310 can rotate about the perpendicular axis (also called the rotational axis) 112

The reamer body 310 also has a first left-hand spiral reamer blade 132a (see, FIGS. 2, 4 to 7). The first left-hand spiral reamer blade 132a has a first cutting edge 350a fluidly extending from a first inclined blade ramp 352a. The first cutting edge 350a and the first inclined blade ramp 352a extend outwardly from the convex curved exterior surface 316 of the reamer body 310. The first inclined blade ramp 352a and the first cutting edge 350a extend from the lower edge 118 to the apex 114. A portion of the first cutting edge 350a, in one embodiment, is positioned over a first left-hand spiral slot 120a, see, FIG. 4's dotted line 101. The first left-hand spiral slot 120a (i) extends from the convex curved exterior surface 316 to the concave curved interior surface 318 (see, FIG. 4) and (ii) is positioned between the lower edge 118 and the apex 114 (see, FIG. 2) while not contacting (a) the lower edge 118 and (b) the apex 114. Additionally, the first left-hand spiral slot 120a has a first leading edge 122a and a first trailing edge 124a. The first trailing edge 124a, compared to the first leading edge 122a, is closer to the first left-hand spiral reamer blade 132a.

The first left-hand spiral slot 120a also has (a) a first length (La) extending from a first proximal end 370a to a first distal end 372a (see, FIG. 5), (b) a first exterior width (Wa) (see, FIG. 4) extending from the first trailing edge 124a to the first leading edge 122a, (c) a first interior width (Ia) extending from a first interior trailing edge 624a to a first interior leading edge 622a wherein (1) the first interior trailing edge 624a can be positioned (i) below the first trailing edge 124a and that is deemed 0° from the first trailing edge 124a (see, FIG. 4), (ii) below the first inclined blade ramp 352a and ranging from +0.1 to +45° in relation to the first trailing edge 124a (see, FIG. 6), (iii) within the first left-hand spiral slot 120a and ranging from −0.1 to −45° in relation to the first trailing edge 124a (see, FIG. 7), or (iv) combinations thereof; and (2) the first interior leading edge 622a can be positioned (i) below the first leading edge 122a that is deemed 0° from the first leading edge 124a, (ii) below the convex curved exterior surface 316 and ranging from −0.1 to −45° in relation to the first leading edge 124a, (iii) within the first left-hand spiral slot 120a and ranging from +0.1 to +45° in relation to the first leading edge 124a, or (iv) combinations thereof; (d) a first apex distance (Aa) between the apex 114 on the convex curved exterior surface 316 and the first distal end 372a, and (e) a first edge distance (Ea) between the first proximal end 370a and the lower edge 118. That means, the angles of the interior trailing edge to the interior leading edge can be +45° to −45° (greatest interior width) to −45° to +45° (narrowest interior width); with the understanding that interior width is normally the same as the exterior width or greater than the exterior width so cut bone chips and/or cut tissue chips can easily pass through the respective slots.

The reamer body 310 also has a second left-hand spiral reamer blade 132b. The second left-hand spiral reamer blade 132b has a second cutting edge 350b fluidly extending from a second inclined blade ramp 352b (see, FIGS. 2, 8, 9, 10, and 11). The second cutting edge 350b and the second inclined blade ramp 352b extend outwardly from the convex curved exterior surface 316 of the reamer body 310. The second inclined blade ramp 352b and the second cutting edge 350b extend from the lower edge 118 toward the apex 114 so the first cutting edge 350a contacts or is within 10 mm of the second cutting edge 350b at the apex 114. A portion of the second cutting edge 350b is positioned over a second left-hand spiral slot 120b. The second left-hand spiral slot 120b (i) extends from the convex curved exterior surface 316 to the concave curved interior surface 318 and (ii) is positioned between the lower edge 118 and the apex 114 while not contacting (a) the lower edge 118 and (b) the apex 114. Additionally, the second left-hand spiral slot 120b has a second leading edge 122b and a second trailing edge 124b. The second trailing edge 124b, compared to the second leading edge 122b, is closer to the second left-hand spiral reamer blade 132b.

The second left-hand spiral slot 120b also has (a) a second length (Lb) extending from a second proximal end 370b to a second distal end 372b, (b) a second exterior width (Wb) extending from the second trailing edge 124b to the second leading edge 122b, (c) a second interior width (Ib) extending from a second interior trailing edge 624a to a second interior leading edge 622b wherein (1) the second interior trailing edge 624b can be positioned below the second trailing edge 124b and that is deemed 0° from the second trailing edge 124b, below the second inclined blade ramp 352b and ranging from +0.1 to +45° in relation to the second trailing edge 124b, within the second left-hand spiral slot 120b and ranging from −0.1 to −45° in relation to the second trailing edge 124b, or combinations thereof; and (2) the second interior leading edge 622b can be positioned below the second leading edge 122b that is deemed 0° from the second leading edge 124b, below the convex curved exterior surface 316 and ranging from −0.1 to −45° in relation to the second leading edge 124b, within the second left-hand spiral slot 120b and ranging from +0.1 to +45° in relation to the second leading edge 124b, or combinations thereof; (d) a second apex distance (Ab) between the apex 114 on the convex curved exterior surface 316 and the second distal end 372b, and (e) a second edge distance (Eb) between the second proximal end 370b and the lower edge 118. That means, the angles of the interior trailing edge to the interior leading edge can be +45° to −45° (greatest interior width) to −45° to +45° (narrowest interior width); with the understanding that interior width is normally the same as the exterior width or greater than the exterior width so cut bone chips and/or cut tissue chips can easily pass through the respective slots.

And when the reamer body rotates and contacts a bone or tissue, the first and second cutting edges 350a, 350b (a) cut bone or cut tissue (900) to create cut bone chips or cut tissue chips, and (b) pushes the cut bone chips or the cut tissue chips toward the apex 114 of the convex curved exterior surface 316 so the cut bone chips or the cut tissue chips break and dislodge free from the bone or the tissue; and then can move toward the lower edge 118 and fall into the slots on the reamer body 310.

It is understood that the first left-hand spiral slot 120a and the second left-hand spiral slot 120b can (a) be identical in length, exterior width, interior width, height, apex distance, and edge distance; (b) have distinct lengths, exterior widths, interior widths, heights, apex distances, and edge distances; or (c) combinations thereof. In most instances, the first left-hand spiral slot 120a and the second left-hand spiral slot 120b are very similar in length, exterior width, interior width, height, apex distance, and edge distance with the understanding that there can be minor differences as a result of the manufacturing process of the reamer body 310.

The reamer body 310 can also, optionally, have at least a third left-hand spiral reamer blade 432c and corresponding third left hand spiral slot 120c and, optionally, a fourth left-hand spiral reamer blade 432d and corresponding fourth left hand spiral slot 120d. The reamer body 310 illustrated shows four-blade configurations since that is an optimal reamer design for the sized reamer being illustrated. That said, the reamer can have a one-blade configuration, a two-blade configuration, a three-blade configuration, the four-blade configuration, or any number of blade configuration that can fit and effectively operate with a particular sized reamer. Obviously, a bigger reamer could have more blade configurations, while a smaller reamer could have less blade configurations. Likewise, the illustrated reamer can have at least the one-blade configuration, the two-blade configuration, the three-blade configuration, the four-blade configuration, or any number of blade configuration.

The third left-hand spiral reamer blade 432c as illustrated in FIGS. 2, and 12-15 has a third cutting edge 450c fluidly extending from a third inclined blade ramp 452c. The third cutting edge 450c and the third inclined blade ramp 452c extend outwardly from the convex curved exterior surface 316 of the reamer body 310. The third inclined blade ramp 452c and the third cutting edge 450c extend from the lower edge 118 toward and not contacting the apex 114 to form a first debris gap 454c positioned between (a) the third reamer blade 432c and (b) the first and second reamer blades 132a, 132b. A portion of the third cutting edge 450c is positioned over a third left-hand spiral slot 120c. The third left-hand spiral slot 120c (i) extends from the convex curved exterior surface 316 to the concave curved interior surface 318 and (ii) is positioned between the lower edge 118 and the apex 114 while not contacting (a) the lower edge 118 and (b) the apex 114. Additionally, the third left-hand spiral slot 120c has a third leading edge 122c and a third trailing edge 124c. The third trailing edge 124c, compared to the third leading edge 122c, is closer to the third left-hand spiral reamer blade 432c.

The third left-hand spiral slot 120c also has (a) a third length (Lc) extending from a third proximal end 370c to a third distal end 372c, (b) a third exterior width (Wc) extending from the third trailing edge 124c to the third leading edge 122c, (c) a third interior width (Ic) extending from a third interior trailing edge 624c to a third interior leading edge 622c wherein (1) the third interior trailing edge 624c can be positioned (i) below the third trailing edge 124c and that is deemed 0° from the third trailing edge 124c, (ii) below the third inclined blade ramp 452c and ranging from +0.1 to +45° in relation to the third trailing edge 124c, (iii) within the third left-hand spiral slot 120c and ranging from −0.1 to −45° in relation to the third trailing edge 124c, or (iv) combinations thereof; and (2) the third interior leading edge 622c can be positioned (i) below the third leading edge 122c that is deemed 0° from the third leading edge 124c, (ii) below the convex curved exterior surface 316 and ranging from −0.1 to −45° in relation to the third leading edge 124c, (iii) within the third left-hand spiral slot 120a and ranging from +0.1 to +45° in relation to the third leading edge 124c, or (iv) combinations thereof; (d) a third apex distance (Ac) between the apex 114 on the convex curved exterior surface 316 and the third distal end 372c, and (e) a third edge distance (Ec) between the third proximal end 370c and the lower edge 118. That means, the angles of the interior trailing edge to the interior leading edge can be +45° to −45° (greatest interior width) to −45° to +45° (narrowest interior width); with the understanding that interior width is normally the same as the exterior width or greater than the exterior width so cut bone chips and/or cut tissue chips can easily pass through the respective slots.

The fourth left-hand spiral reamer blade 432d (see, FIGS. 2, and 16 to 19) has a fourth cutting edge 450d fluidly extending from a fourth inclined blade ramp. The fourth cutting edge 450d and the fourth inclined blade ramp 452d extend outwardly from the convex curved exterior surface 316 of the reamer body 310, and there can be spacing in the blade ramp or a mirror-image of the third left-hand spiral reamer blade 432c. The fourth inclined blade ramp 452d and the fourth cutting edge 450d extend from the lower edge 118 toward and not contacting the apex 114 to form a second debris gap 454d positioned between (a) the fourth reamer blade 432d and (b) the first and second reamer blades 132a, 132b. A portion of the fourth cutting edge 450d is positioned over a fourth left-hand spiral slot 120d. The fourth left-hand spiral slot 120d (i) extends from the convex curved exterior surface 316 to the concave curved interior surface 318 and (ii) is positioned between the lower edge 118 and the apex 114 while not contacting (a) the lower edge 118 and (b) the apex 114. Additionally, the fourth left-hand spiral slot 120d has a fourth leading edge 122d and a fourth trailing edge 124d. The fourth trailing edge 124d, compared to the fourth leading edge 122d, is closer to the fourth left-hand spiral reamer blade 432d.

The fourth left-hand spiral slot 120d also has (a) a fourth length (Ld) extending from a fourth proximal end 370d to a fourth distal end 372d, (b) a fourth exterior width (Wd) extending from the fourth trailing edge 124d to the fourth leading edge 122d, (c) a fourth interior width (Id) extending from a fourth interior trailing edge 624d to a fourth interior leading edge 622d wherein (1) the fourth interior trailing edge 624d can be positioned (i) below the fourth trailing edge 124d and that is deemed 0° from the fourth trailing edge 124a, (ii) below the fourth inclined blade ramp 452d and ranging from +0.1 to +45° in relation to the fourth trailing edge 124d, (iii) within the fourth left-hand spiral slot 120d and ranging from −0.1 to −45° in relation to the fourth trailing edge 124d, or (iv) combinations thereof; and (2) the fourth interior leading edge 622d can be positioned (i) below the fourth leading edge 122d that is deemed 0° from the fourth leading edge 124d, (ii) below the convex curved exterior surface 316 and ranging from −0.1 to −45° in relation to the fourth leading edge 124d, (iii) within the fourth left-hand spiral slot 120d and ranging from +0.1 to +45° in relation to the fourth leading edge 124d, or (iv) combinations thereof; (d) a fourth apex distance (Ad) between the apex 114 on the convex curved exterior surface 316 and the fourth distal end 372d, and (e) a fourth edge distance (Ed) between the fourth proximal end 370d and the lower edge 118. That means, the angles of the interior trailing edge to the interior leading edge can be +45° to −45° (greatest interior width) to −45° to +45° (narrowest interior width); with the understanding that interior width is (a) normally the same as the exterior width or (b) greater than the exterior width so cut bone chips and/or cut tissue chips can easily pass through the respective slots.

When the reamer body 310 rotates and contacts a bone or tissue, the first cutting edge 350a, the second cutting edge 350b, the third cutting edge 450c, and the fourth cutting edge 450d (a) cut bone or tissue to create cut bone chips or cut tissue chips, and (b) pushes the cut bone chips or the cut tissue chips toward the apex 114 of the convex curved exterior surface 316 so the cut bone chips or the cut tissue chips break and dislodge free from the bone or the tissue. That means, the cut bone chips or the cut tissue chips do not always fall into the slot 120a, 120b, 120c, 120d that correlates with the cutting edge 350a, 350b, 450c, 450d that created the cut bone chips and/or cut tissue chips.

It is understood that the third left-hand spiral slot 120c and the fourth left-hand spiral slot 120d can (a) be identical in length, exterior width, interior width, height, apex distance, and edge distance; (b) have distinct lengths, exterior widths, interior widths, heights, apex distances, and edge distances; or (c) combinations thereof. In most instances, the third left-hand spiral slot 120c and the fourth left-hand spiral slot 120d are very similar in length, exterior width, interior width, height, apex distance, and edge distance with the understanding that there can be minor differences as a result of the manufacturing process of the reamer body 310.

It is understood that the first, second, third and fourth left-hand spiral slots 120a, 120b, 120c, 120d can (a) be identical in length, exterior width, interior width, height, apex distance, and edge distance; (b) have distinct lengths, exterior widths, interior widths, heights, apex distances, and edge distances; or (c) combinations thereof. In most instances, the first, second, third and fourth left-hand spiral slots 120a, 120b, 120c, 120d are very similar in length, exterior width, interior width, height, apex distance, and edge distance with the understanding that there can be minor differences as a result of the manufacturing process of the reamer body 310.

Likewise, the first debris gap 454c and the second debris gap 454d can be identical in area, width, and length; or distinct from each other. In most instances, the first debris gap 454c and the second debris gap 454d are very similar in area, length, and width with the understanding that there can be minor differences as a result of the manufacturing process of the reamer body 310.

The first inclined blade ramp 352a extends outwardly from the convex curved exterior surface 316 of the reamer body 310. The first inclined blade ramp 352a has (a) a first ramp leading edge 550a that has the first cutting edge 350a, and (b) a first ramp trailing edge 552a that is separated from the ramp leading edge 550 by a first predetermined distance 554a. That first predetermined distance 554a ranges from 1 mm to 20 mm. Starting from the first ramp trailing edge 552a, the first inclined blade ramp 352a extends outwardly from the convex curved exterior surface 316 of the reamer body 310 to or toward the first ramp leading edge 550a at an angle that ranges from about 1° to about 30° as measured from the first incline blade ramp 352a to a tangent plane 902a from the first ramp trailing edge 552a, which forms a first chip wall 700a that can guide the cut bone and cut tissue 900 into a slot 120a-d. In addition, the first inclined blade ramp 352a positioned between the first ramp trailing edge 552a and the first ramp leading edge 550a can be (a) a planar surface, (b) a convex curved surface that essentially parallels the convex curved exterior surface 316, (c) a concave curved surface, or (d) combinations thereof.

The second inclined blade ramp 352b extends outwardly from the convex curved exterior surface 316 of the reamer body 310. The second inclined blade ramp 352b has (a) a second ramp leading edge 550b that has the second cutting edge 350b, and (b) a second ramp trailing edge 552b that is separated from the second ramp leading edge 550b by a second predetermined distance 554b. That second predetermined distance 554b ranges from 1 mm to 20 mm. Starting from second ramp trailing edge 552b, the second inclined blade ramp 352b extends outwardly from the convex curved exterior surface 316 of the reamer body 310 to or toward the second ramp leading edge 550b at an angle that ranges from about 1° to about 30° as measured from the second incline blade ramp 352b to a tangent plane 902b from the second ramp trailing edge 552b, which forms a second chip wall 700b that can guide the cut bone and cut tissue 900 into a slot 120a-d. In addition, the second inclined blade ramp 352b positioned between the second ramp trailing edge 552b and the second ramp leading edge 550b can be (a) a planar surface, (b) a convex curved surface that essentially parallels the convex curved exterior surface 316, (c) a concave curved surface, or (d) combinations thereof.

The third inclined blade ramp 352c extends outwardly from the convex curved exterior surface 316 of the reamer body 310. The third inclined blade ramp 352c has (a) a third ramp leading edge 550c that has the third cutting edge 350c, and (b) a third ramp trailing edge 552c that is separated from the third ramp leading edge 550c by a third predetermined distance 554c. That third predetermined distance 554b ranges from 1 mm to 20 mm. Starting from third ramp trailing edge 552c, the third inclined blade ramp 352c extends outwardly from the convex curved exterior surface 316 of the reamer body 310 to or toward the third ramp leading edge 550c at an angle that ranges from about 1° to about 30° as measured from the third incline blade ramp 352c to a tangent plane 902c from the third ramp trailing edge 552c, which forms a third chip wall 700c that can guide the cut bone and cut tissue 900 into a slot 120a-d. In addition, the third inclined blade ramp 352c positioned between the third ramp trailing edge 552c and the third ramp leading edge 550c can be (a) a planar surface, (b) a convex curved surface that essentially parallels the convex curved exterior surface 316, (c) a concave curved surface, or (d) combinations thereof.

The fourth inclined blade ramp 352d extends outwardly from the convex curved exterior surface 316 of the reamer body 310. The fourth inclined blade ramp 352d has (a) a fourth ramp leading edge 550d that has the fourth cutting edge 350d and (b) a fourth ramp trailing edge 552d that is separated from the fourth ramp leading edge 550d by a fourth predetermined distance 554d. That fourth predetermined distance 554d ranges from 1 mm to 20 mm. Starting from fourth ramp trailing edge 552d, the fourth inclined blade ramp 352d extends outwardly from the convex curved exterior surface 316 of the reamer body 310 to or toward the fourth ramp leading edge 550d at an angle that ranges from about 1° to about 30° as measured from the fourth incline blade ramp 352d to a tangent plane 902d from the fourth ramp trailing edge 552d, which forms a fourth chip wall 700d that can guide the cut bone and cut tissue 900 into a slot 120a-d. In addition, the fourth inclined blade ramp 352d positioned between the fourth ramp trailing edge 552d and the fourth ramp leading edge 550d can be (a) a planar surface, (b) a convex curved surface that essentially parallels the convex curved exterior surface 316, (c) a concave curved surface, or (d) combinations thereof.

The first chip wall 700a, the second chip wall 700b, the third chip wall 700c, the fourth chip wall 700d can also be (a) a planar surface, (b) a convex surface, (c) a concave surface, or (d) combinations thereof. Also, the first chip wall 700a, the second chip wall 700b, the third chip wall 700c, the fourth chip wall 700d, each has a proximal end 702 that contacts the convex curved exterior surface 316 and extends, respectively, to the first ramp leading edge 550a, the second ramp leading edge 550b, the third ramp leading edge 550c, and the fourth ramp leading edge 550d. In many embodiments, that proximal end 702 contacts the respective trailing edge 124a-d. When a cliff wall tangent line 101 is positioned at the proximal end 702, the respective chip wall 700 when analyzed from the proximal end 702 to the respective ramp leading edge 550 can be perpendicular to the cliff wall tangent line 101, angled over the corresponding slot between +45 to +89.9° in relation to the cliff wall tangent line 101, or angled over the convex curved exterior surface 316 between −45 to −89.9° in relation to the cliff wall tangent line 101.

It is understood that the first predetermined distance 554a can have a uniform first predetermined distance as the first inclined blade ramp 352a extends from the lower edge 118 toward the apex 114 or a varied or tapered first predetermined distance 554a as the first inclined blade ramp 352a extends from the lower edge 118 toward the apex 114. In most instances, the first predetermined distance 554a is a uniform distance with the understanding that there can be minor differences as a result of the manufacturing process of the reamer body 310.

It is also understood that the second predetermined distance 554b can have a uniform second predetermined distance 554b as the second inclined blade ramp 352b extends from the lower edge 118 toward the apex 114 or a varied or tapered second predetermined distance 554b as the second inclined blade ramp 352b extends from the lower edge 118 toward the apex 114. In most instances, the second predetermined distance 554b is a uniform distance with the understanding that there can be minor differences as a result of the manufacturing process of the reamer body 310.

The lower edge 118 of the reamer body 310 resides along an imaginary equatorial plane 119. From that understanding, there can be a plurality of imaginary horizontal planes positioned parallel to the imaginary equatorial plane 119 that extend from the lower edge 118 to the apex 114.

It is also understood the first predetermined distance 554a along the imaginary equatorial plane 119 and the second predetermined distance 554b along the imaginary equatorial plane 119 can be identical—or there can be minor differences as a result of the manufacturing process of the reamer body 310. Understanding that the first and second predetermined distances 554a, 554b could also be tapered as the first and second inclined blade ramps 352a, 352b extend from the lower edge 118 toward the apex 114.

Figure 3A:
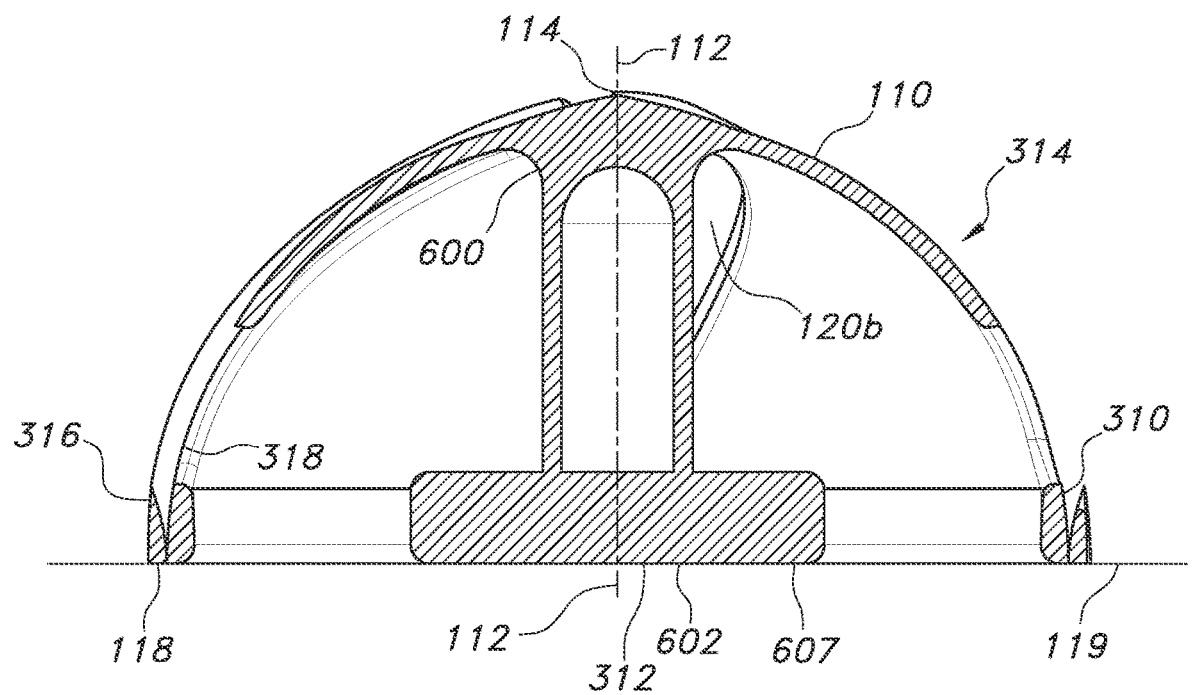
FIGS. 3A-3E illustrate a cross-sectional view of different embodiments of the acetabular reaming tool of FIG. 2 taken along lines 3-3.
Figure 3B:
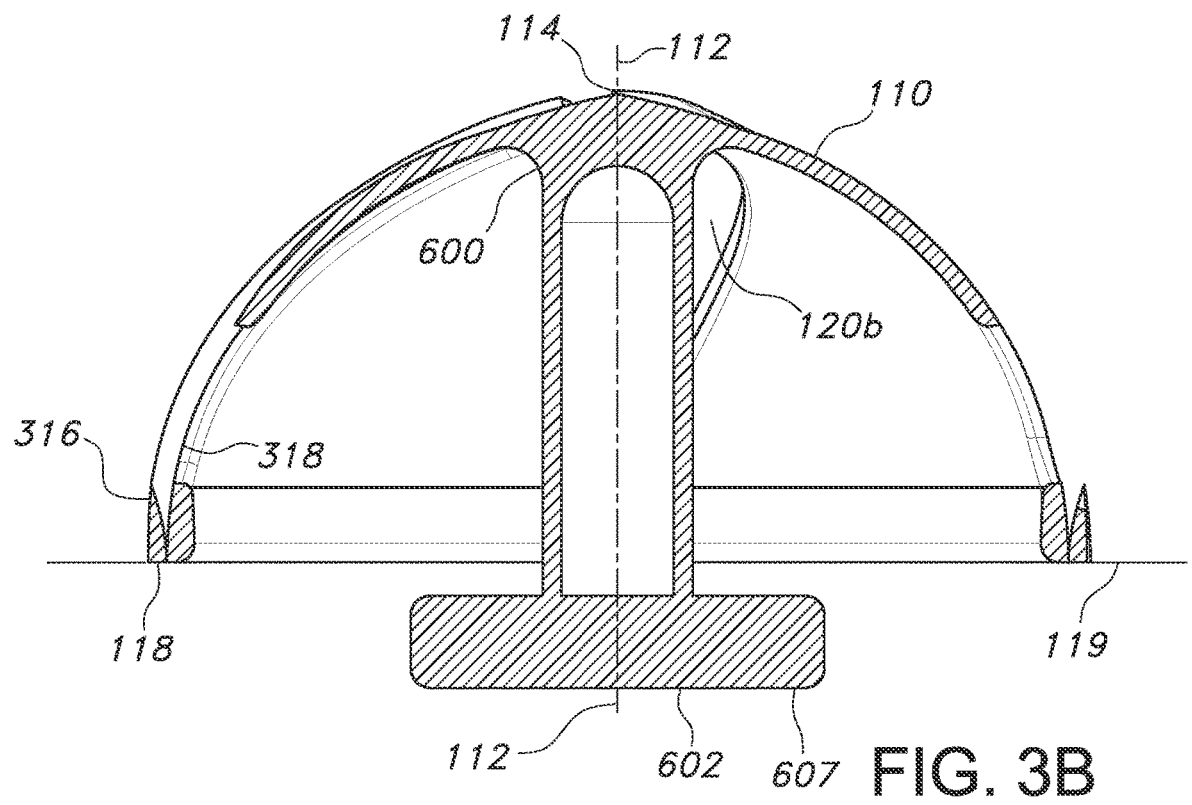
Figure 3C:
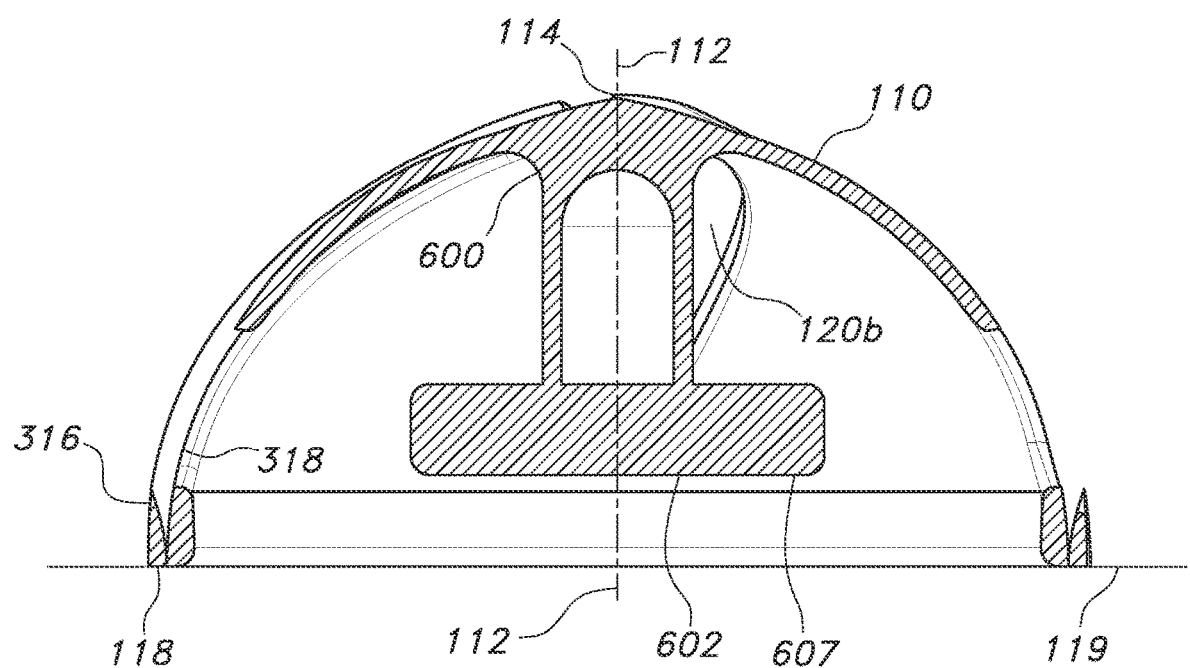
Figure 3D:
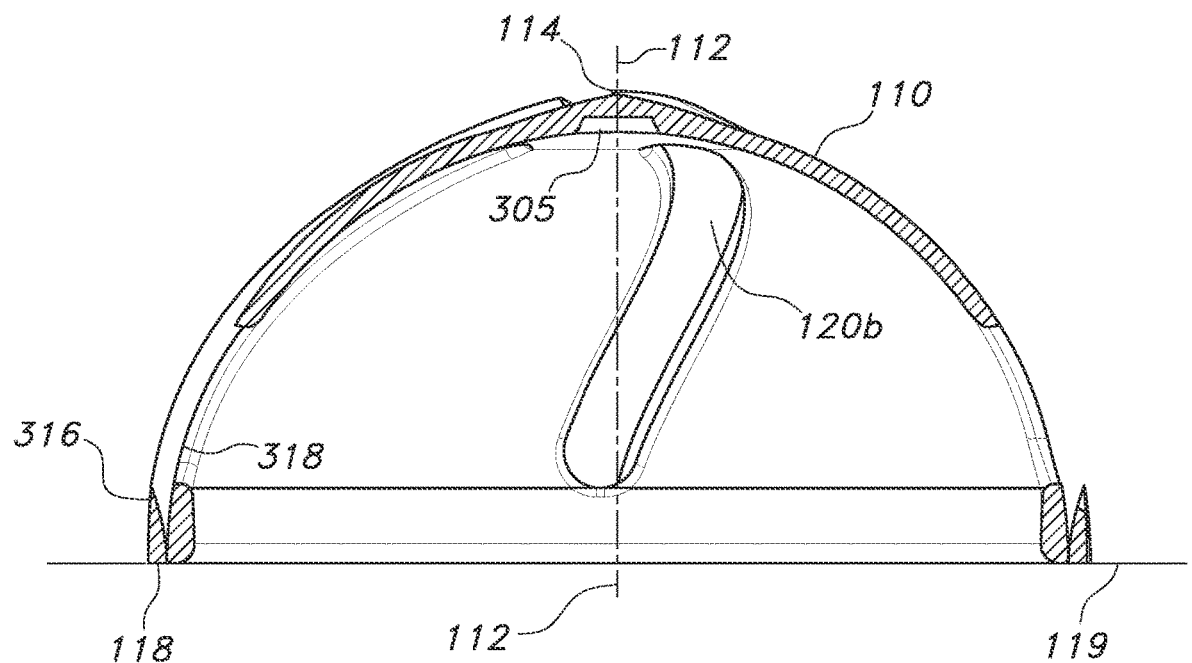
Figure 3E:
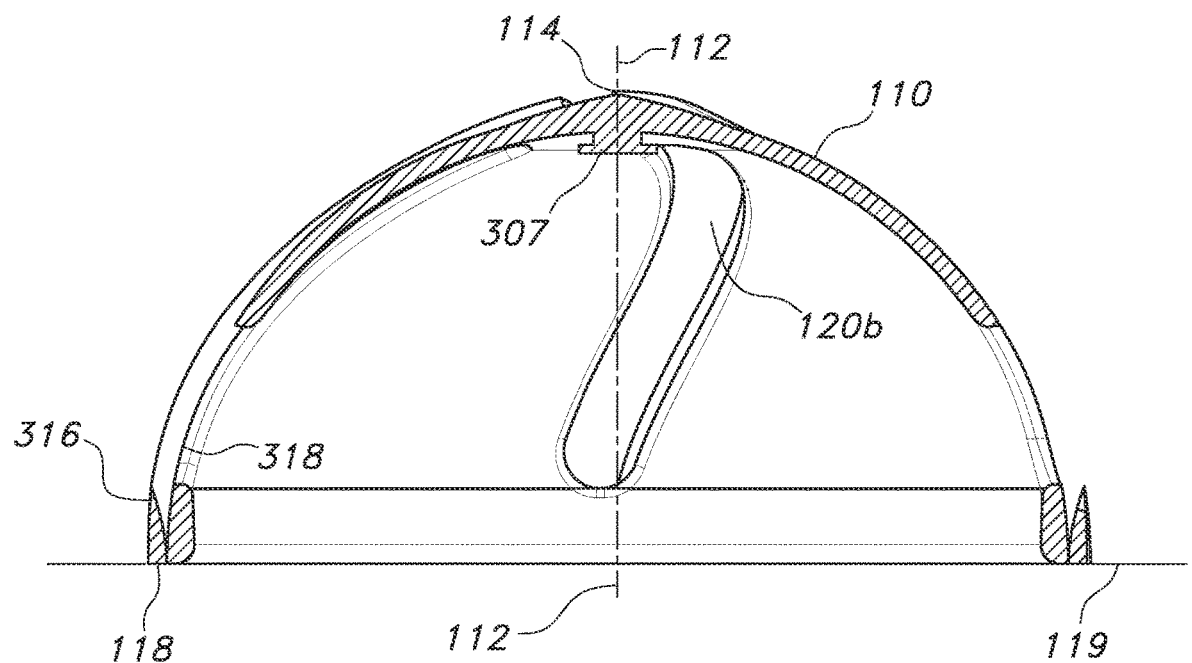
Figure 4:
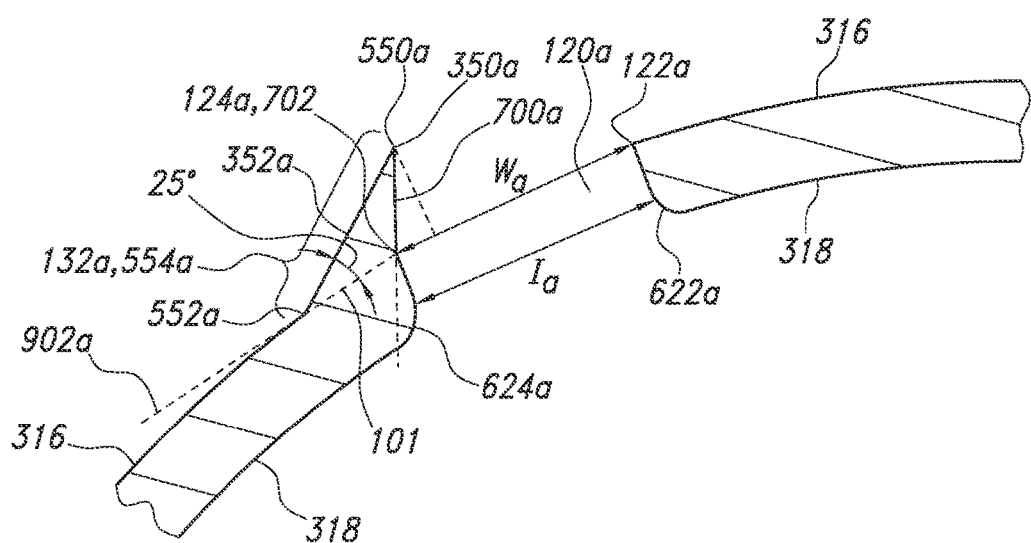
FIG. 4 illustrates FIG. 2 taken along lines 4-4.
Figure 5:
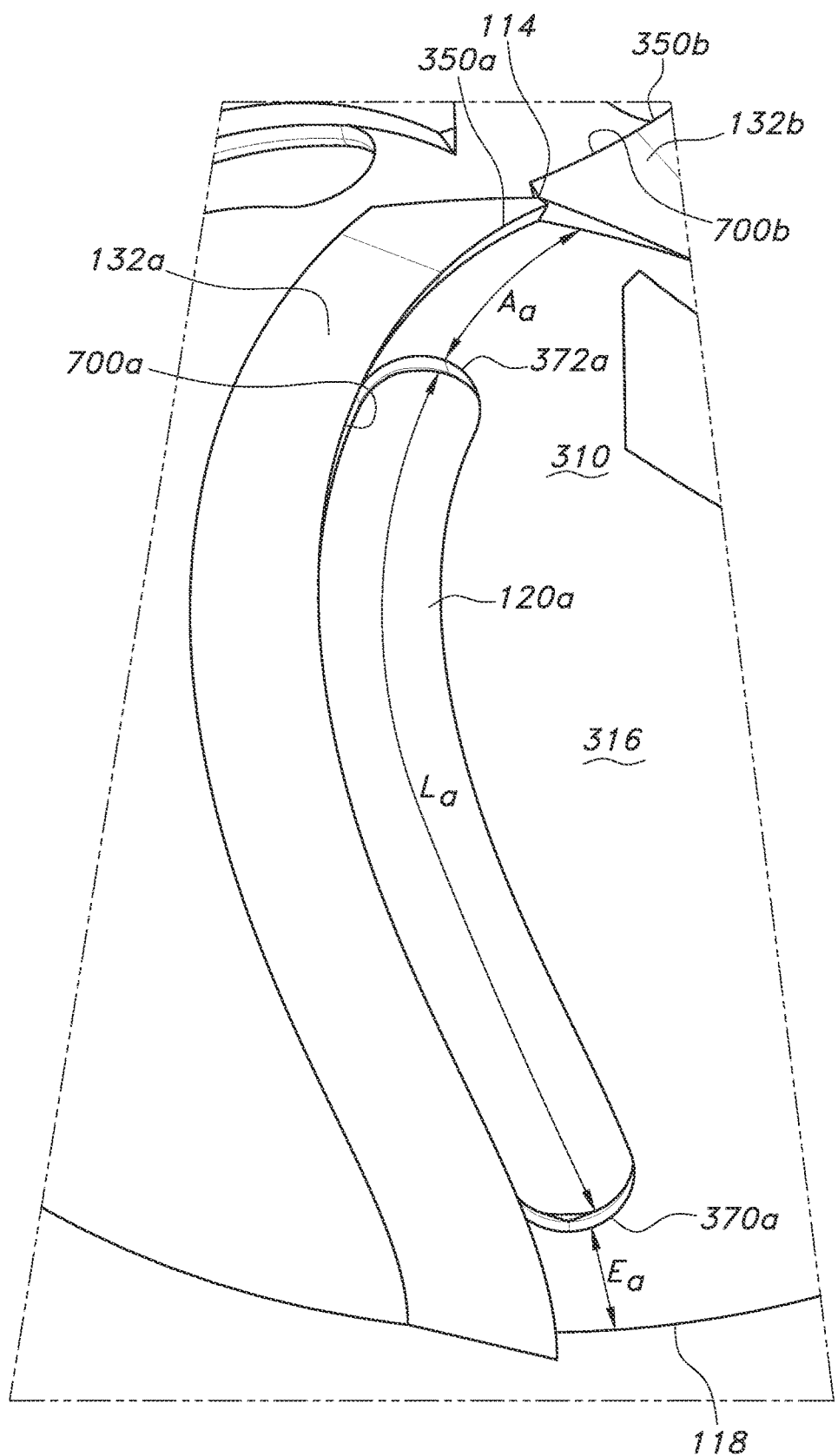
FIG. 5 illustrates FIG. 2 taken from box 5.
Figure 6:
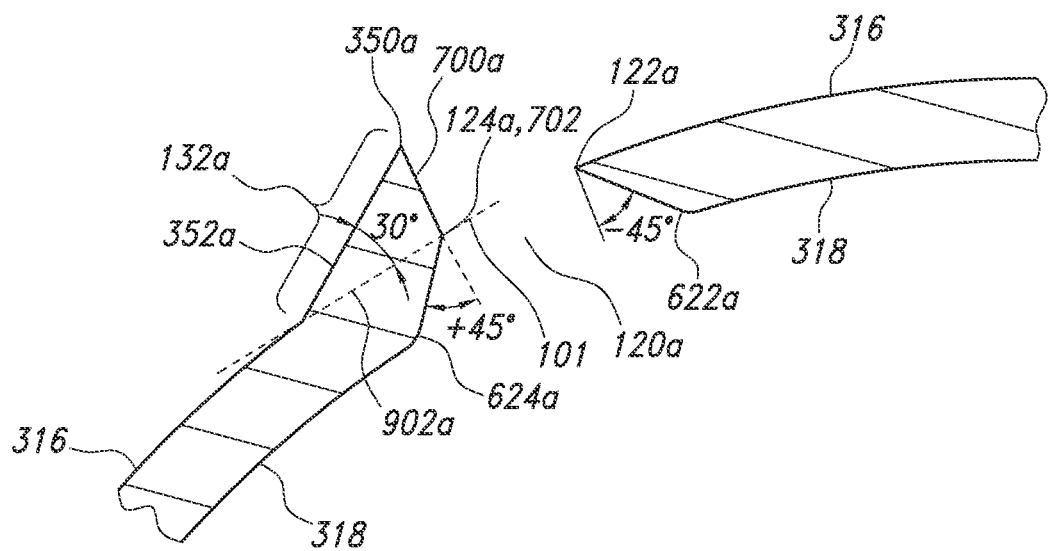
FIG. 6 illustrates an alternative embodiment of FIG. 4.
Figure 7:
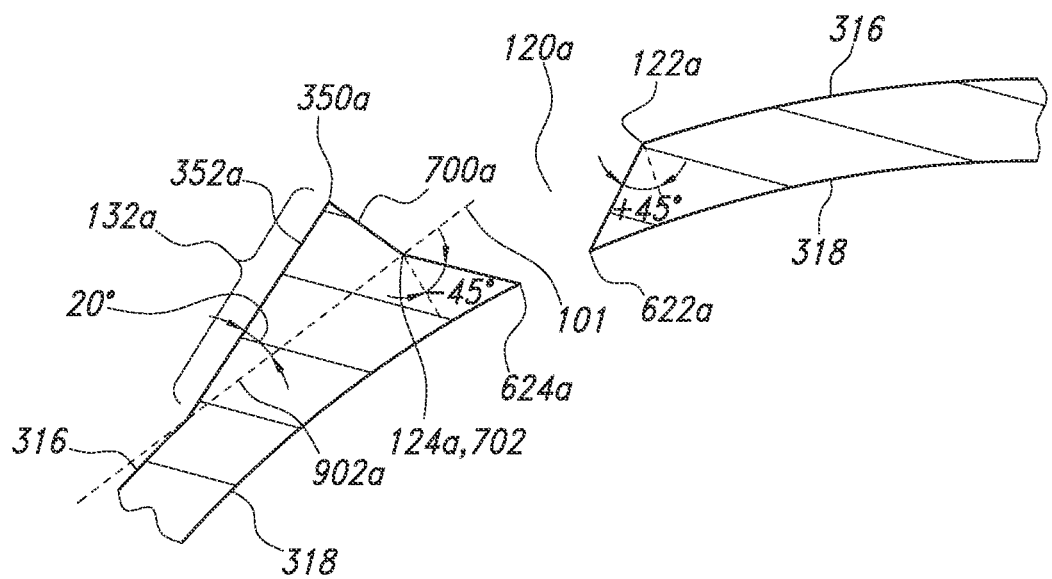
FIG. 7 illustrates an alternative embodiment of FIG. 4.
Figure 8:
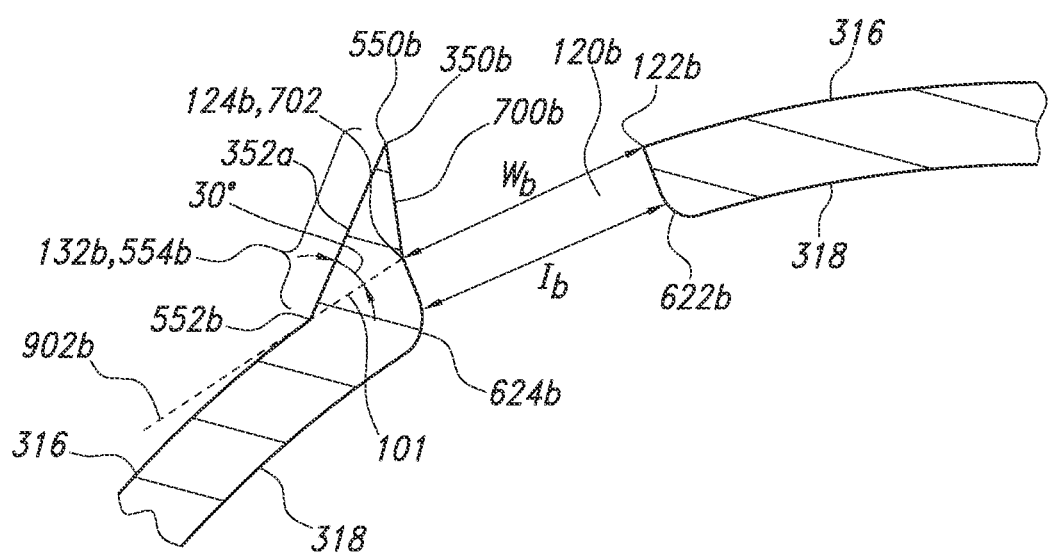
FIG. 8 illustrates FIG. 2 taken along lines 8-8.
Figure 9:
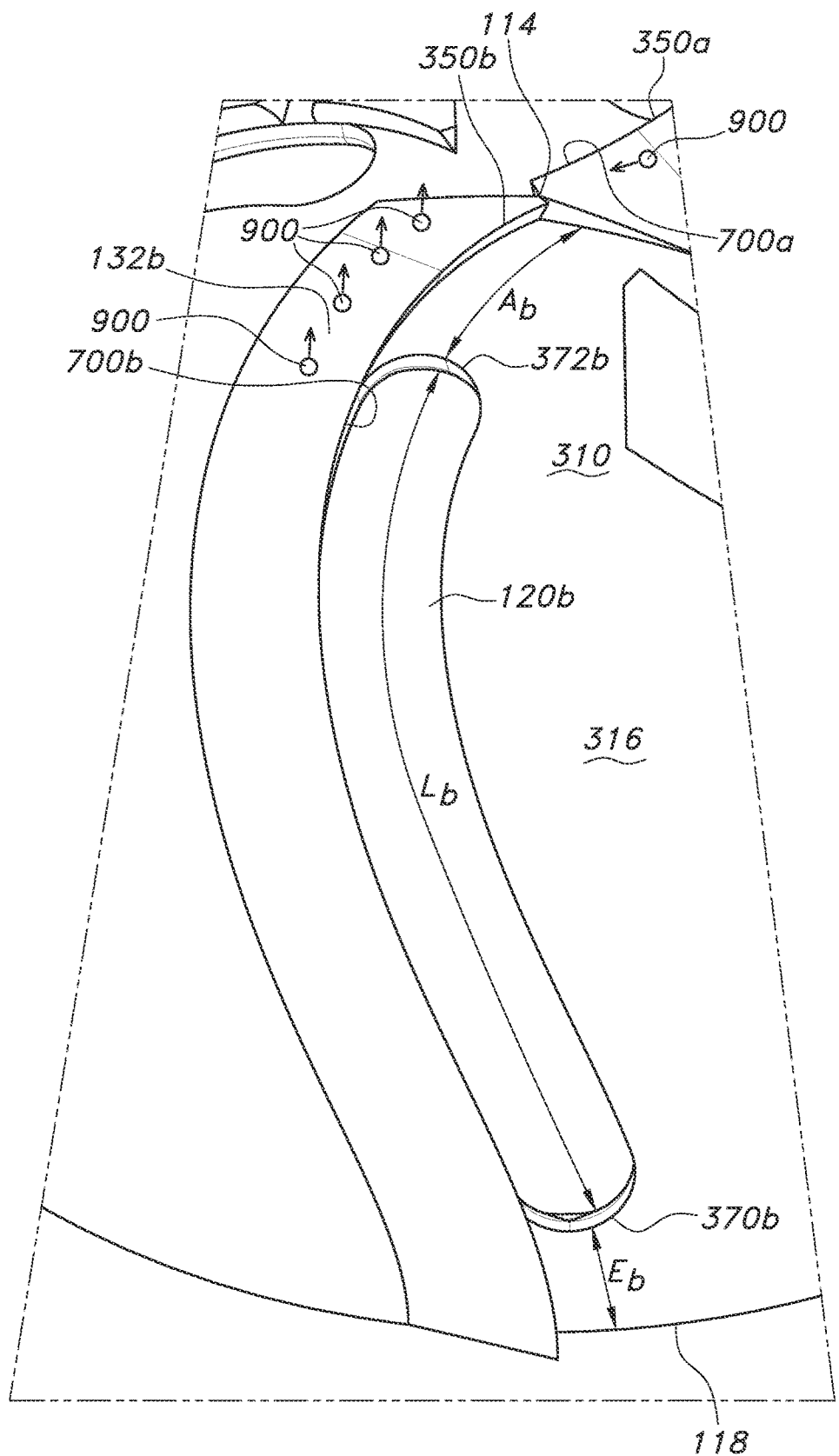
FIG. 9 illustrates FIG. 2 taken from box 9.
Figure 10:
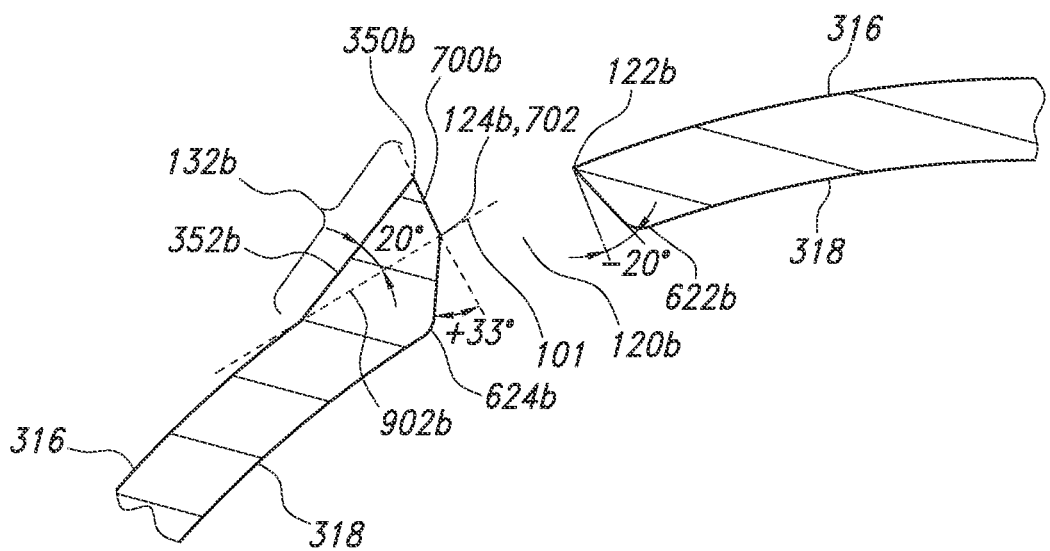
FIG. 10 illustrates an alternative embodiment of FIG. 8.
Figure 11:
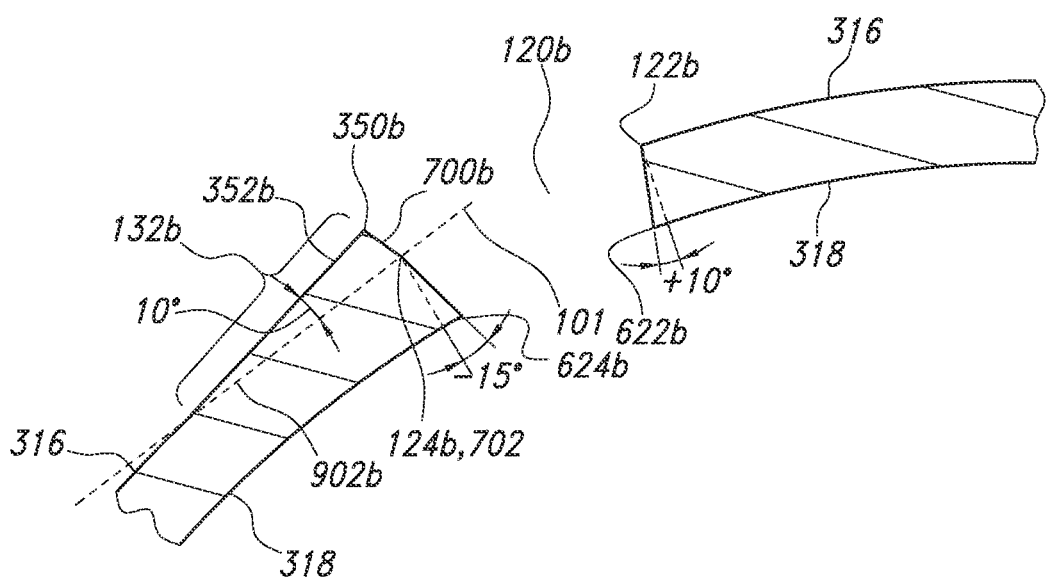
FIG. 11 illustrates an alternative embodiment of FIG. 8.
Figure 12:
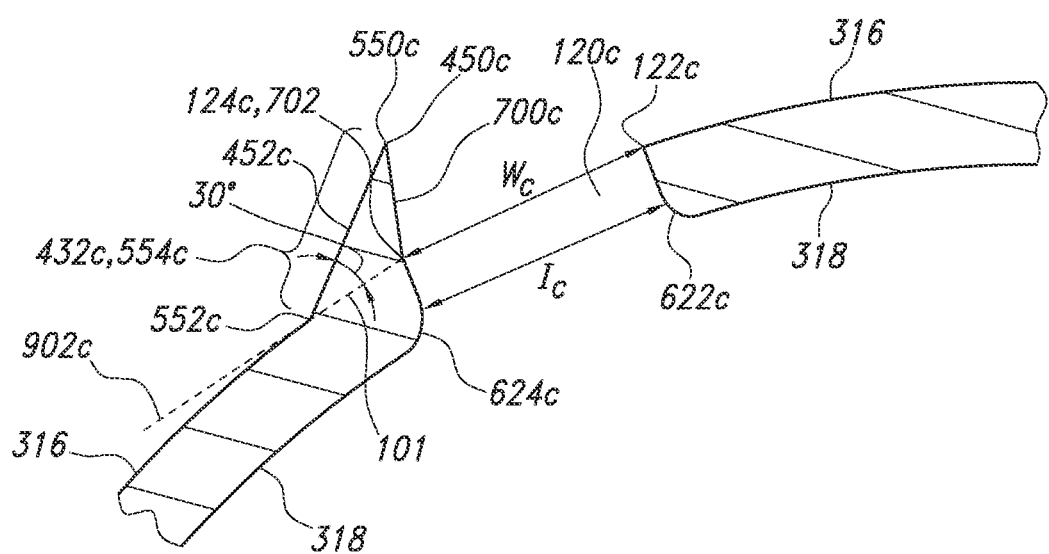
FIG. 12 illustrates FIG. 2 taken along lines 12-12.
Figure 13:
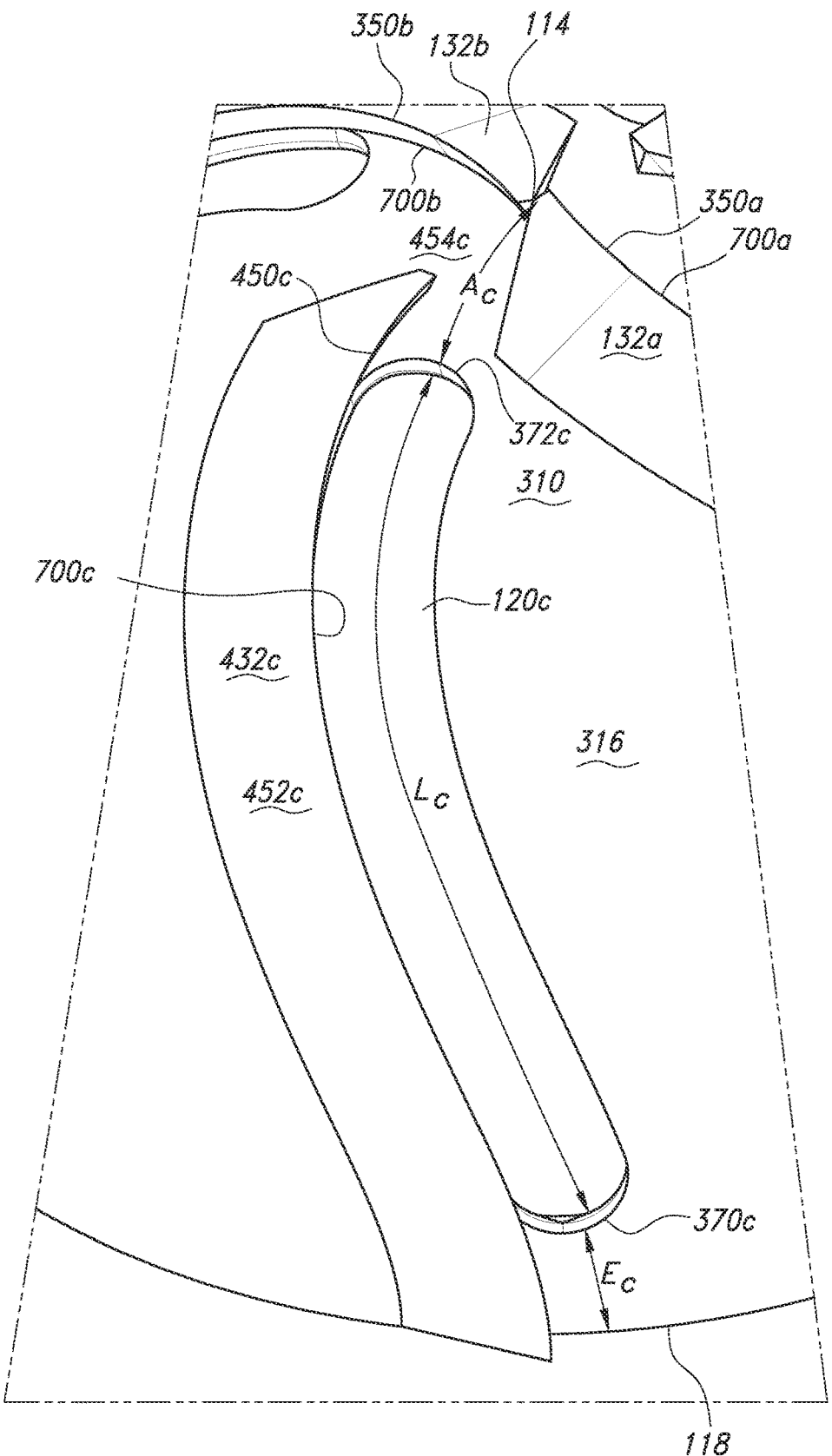
FIG. 13 illustrates FIG. 2 taken from box 13.
Figure 14:
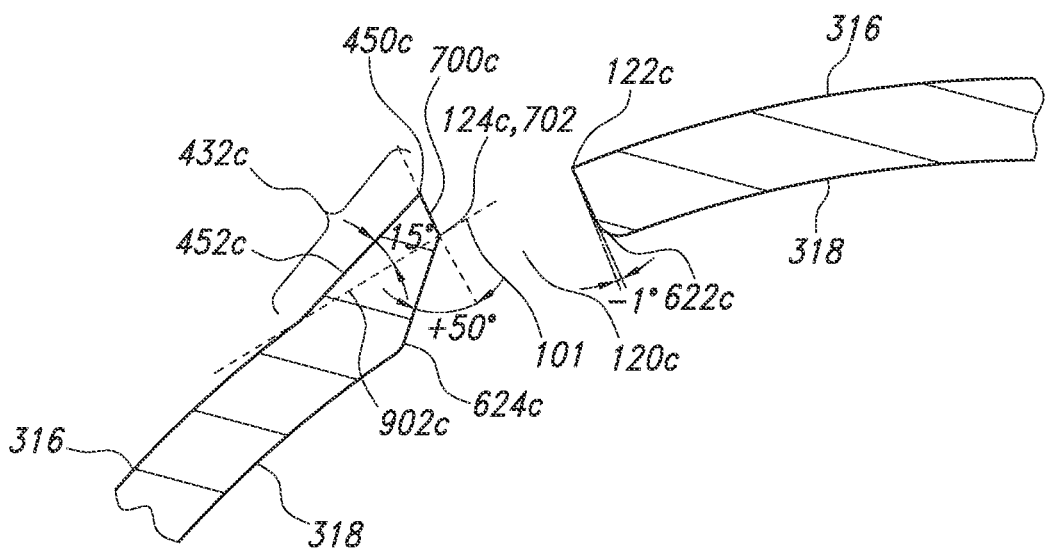
FIG. 14 illustrates an alternative embodiment of FIG. 12.
Figure 15:
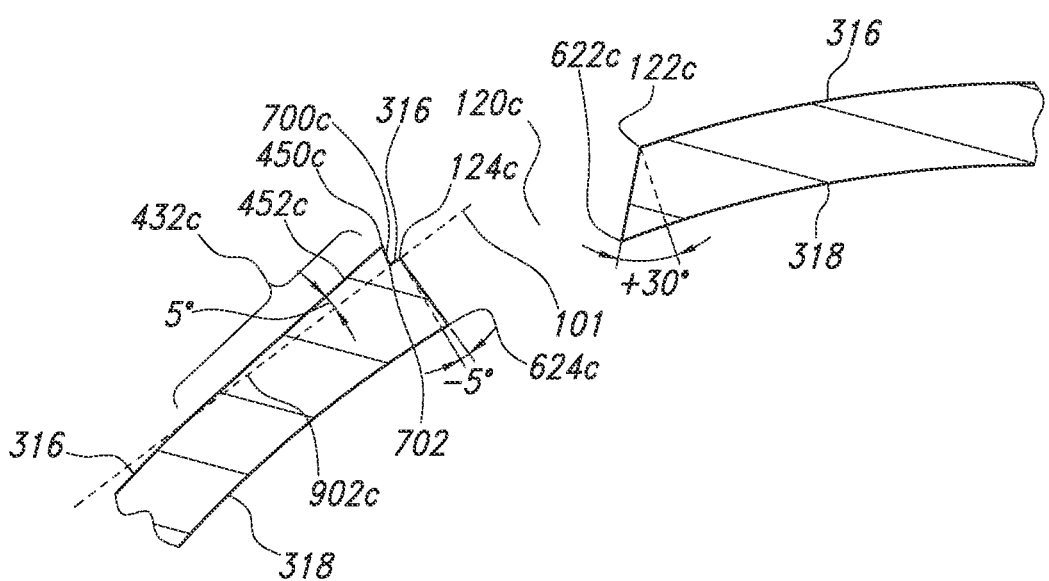
FIG. 15 illustrates an alternative embodiment of FIG. 12.
Figure 16:
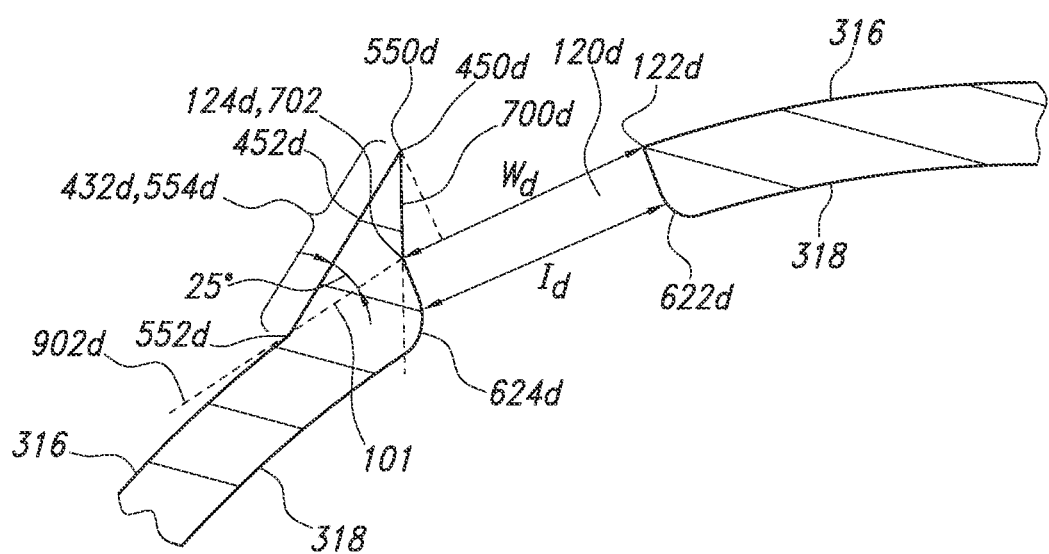
FIG. 16 illustrates FIG. 2 taken along lines 10-10.
Figure 17:
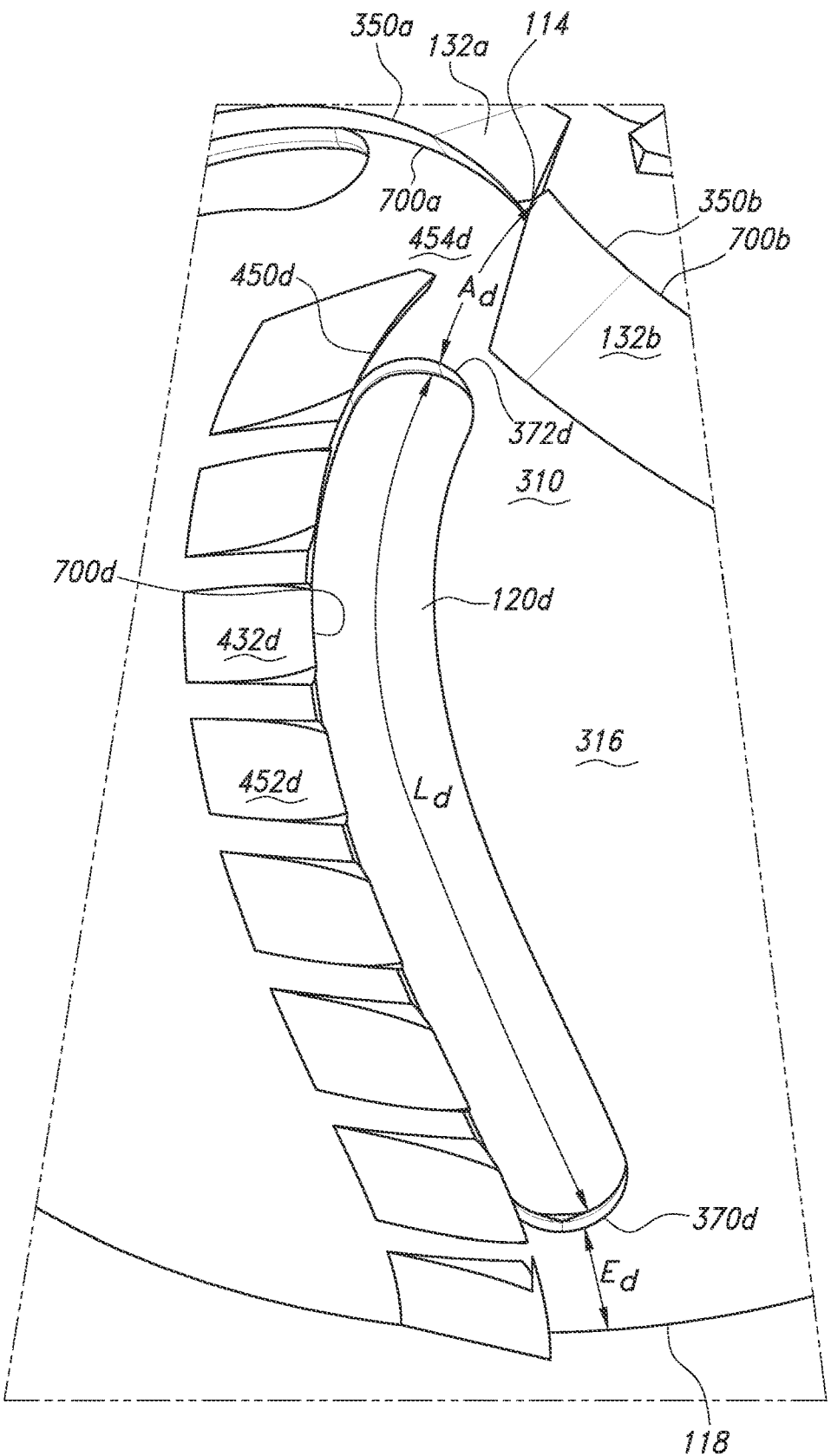
FIG. 17 illustrates FIG. 2 taken from box 17.
Figure 18:
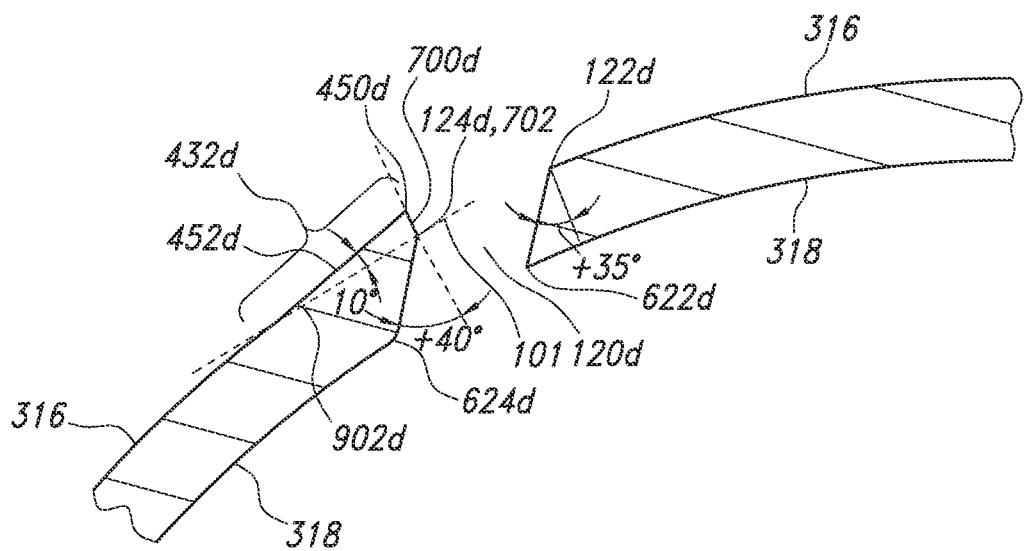
FIG. 18 illustrates an alternative embodiment of FIG. 16.
Figure 19:
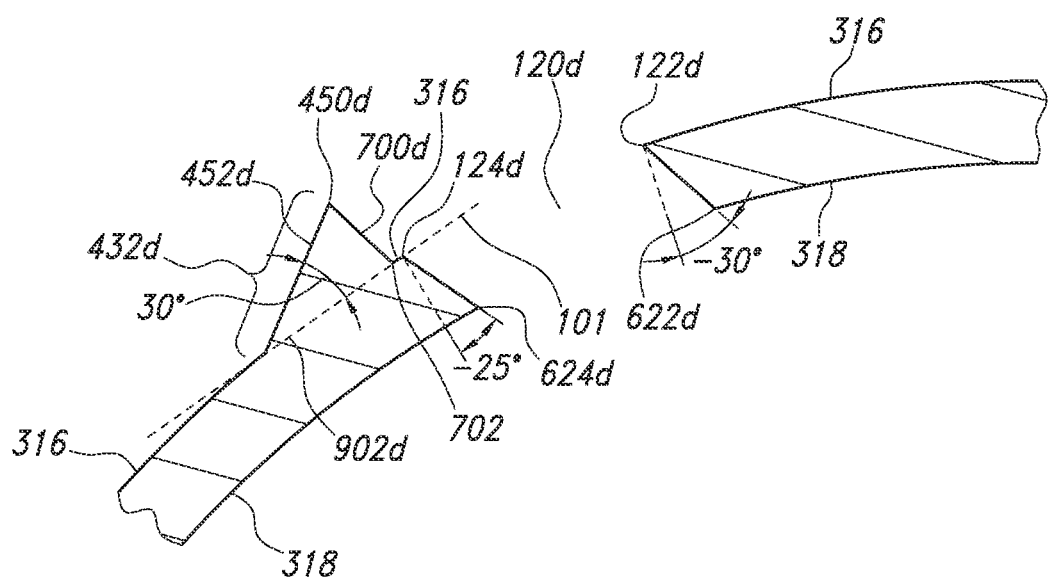
FIG. 19 illustrates an alternative embodiment of FIG. 16.

The reamer shaft 312 has a distal end 600, as shown in FIGS. 3a-c, extending downward along the perpendicular axis 112 from the apex 114 of the concave curved interior surface 318 (a) toward the imaginary equatorial plane 119, (b) toward the imaginary equatorial plane 119 and terminating at the imaginary equatorial plane 119, or (c) toward the imaginary equatorial plane 119 and extending beyond the imaginary equatorial plane.

A conventional surgical driver can attach to the reamer shaft 312. The reamer shaft 312 can be a solid material, a hollow cylinder shape, or combinations thereof. The reamer shaft 312 also has a proximal end 602. The proximal end 602 can have at least one slit, at least one slot or at least one interconnection rod 607 or combination thereof so the conventional surgical driver can attach to the reamer shaft 312. The at least one interconnection rod can have any configurations illustrated as orthogonal bars in U.S. Pat. No. 10,660,658; or extending from or near the proximal end 602. In some embodiments, the at least one interconnection rod (a) is parallel to or in the same plane as the imaginary equatorial plane 119 and (b) extends toward the concave curved interior surface 318. Due to how the reamer 310 is manufactured, the at least one interconnection rod does not contact the concave curved interior surface 318.

The substantially hemispherical and hollow cutting head 110 including the reamer body, the reamer shaft, first left-hand spiral reamer blade, second left-hand spiral reamer blade, third left-hand spiral reamer blade, and fourth left-hand spiral reamer blade are made of the same material selected from the group consisting of stainless steel, cobalt chrome, titanium, carbon fiber reinforced plastic, and combinations thereof. That material can be formed into the desired shape—a reamer—by a three-dimensional metal binder jetting printing process. There is the possibility that there could be residual binder material from the three-dimensional metal binder jetting printing process in the reamer product that is used as a reamer. It is understood that such binder material should be removed but there is a chance that some residual binder material could be found in the reamer product that is used as a reamer.

A preferred production process used to manufacture the entire substantially hemispherical and hollow cutting head 110 is commonly referred to as metal binder jet technology. It is understood that the machine used in metal binder jet technology uses rollers to distribute a thin even layer of metal powder and subsequently prints binder on the layer using a printer head similar to an ink jet printing process. The printed binder defines a cross section of the substantially hemispherical and hollow cutting head 110 on each applied layer. After forming the base printed binder-metal layer, the machine distributes another layer of powder over the base printed binder-metal layer and the binder process repeats to create the desired cross-section for the substantially hemispherical and hollow cutting head 110. That process of layering and binding is repeated for each cross-sectional layer until the desired substantially hemispherical and hollow cutting head 110 shape is eventually created in a build envelope. When finished the build envelope is filled with free powder and at least the bound powder object in the form of the substantially hemispherical and hollow cutting head. The free powder is removed (manually—preferably—or mechanically through tools, gases, liquids, or combinations thereof) and the result is at least one bound metal part is formed and that at least one bound metal part is commonly referred to as a green part. Each green part then follows the same process flow as a metal injection molded part wherein the binder is removed. Examples of that process flow include and are not limited to:

Curing, wherein curing increases the strength of the green parts so green parts can be safely removed from the printing bed (or build envelope). During the process the green parts are hardened off in an oven at roughly 200° C. for a period of several hours, resulting in much stronger parts.

Despite the curing, the green parts may still be highly porous. To reduce the porosity of the green parts, the green parts can undergo a sintering or infiltration process.

Typically, the sintering process takes place in a furnace with a controlled atmosphere, where the green part is heat treated at roughly 100° C. for 24 to 36 hours and the binding agent is burnt away. The sintering process assists in fusing the metal particles together and results in a strong metal part with a low porosity. Sintering, however, can cause non-homogenous shrinkage to the part and can be hard to predict—this must therefore be taken into consideration at the design stage.

To achieve high density, the green part may need to be infiltrated to fill voids left by the binding agent being burnt away during the curing process. The infiltration process is usually performed by applying molten bronze to the green part in order for the molten bronze to infiltrate the voids in the green part. Undergoing these post-processing steps can significantly enhance the mechanical properties of the metal part; for example, bronze infiltration of stainless steel can achieve a final density of 95%.

Finally, although optional, the part can be polished and plated with gold or nickel allowing aesthetically pleasing surface finishes.

The resulting sintered part is greater than 95% of the theoretical density and can then be processed by traditional metal working processes. In the case of a reamer, the reamer may be (A) heat treated to increase the reamer's hardness, (B) be tumbled or blasted to smooth out the finish, (C) ground to increase the blades' (cutting edge 132) sharpness, (D) coated with traditional processes of a biomedical compatible compound(s) to (i) color code the reamer to identify a specific size, make, or combinations thereof; (ii) increase the reamer's resistance to wear, (iii) reduce the reamer's surface tension so that the reamer will not watermark from an autoclaving processes, and (iv) combinations thereof; and (E) combinations thereof. Coating the reamer with biomedical compatible compound(s) is normally a thin coating having a layer thickness in the range between 0.5 and 1.8 µm. A PVD (physical vapor deposition) process is suitable for application of the thin coating. It is understood the biomedical compatible compound(s) can be any compound or combination of compounds that accomplish the above-identified objectives and simultaneously do not adversely affect a patient. The use of the metal binder jet allows the parts to be printed with extreme complexity and accuracy that could not be matched economically with traditional metal working or forming processes.

It is understood that in some embodiments, a portion of each cutting edge 132 is positioned over its respective slot 120, and does not extend over the slot's center line 154 in order to maximize the material being cut by the cutting edge 132.

The reamer may be disposable or not. The reamer may be cleaned through an autoclaving process; or repeatedly cleaned through an autoclaving process.

In addition, it is understood that each blade (cutting edge) and slot set on the substantially hemispherical and hollow cutting head 110 is spaced a distance from other blade and slot sets on the substantially hemispherical and hollow cutting head 110. In most instances, if there are two blade and slot sets on the substantially hemispherical and hollow cutting head 110, then each blade and slot set is 180° from each other. Likewise, if there are three blade and slot sets on the substantially hemispherical and hollow cutting head 110, then each blade and slot set is 120° from each other. Similarly, if there are four blade and slot sets on the substantially hemispherical and hollow cutting head 110, then each blade and slot set is 90° from the adjacent blade and slot set.

It will be understood that well known processes have not been described in detail and have been omitted for brevity. Although specific steps, structures and materials may have been described, the present disclosure may not be limited to these specifics, and others may substitute as is well understood by those skilled in the art, and various steps may not necessarily be performed in the sequences shown.

While this disclosure has described certain embodiments and generally associated methods, alterations and permutations of these embodiments and methods will be apparent to those skilled in the art. Accordingly, the above description of example embodiments does not define or constrain this disclosure. Other changes, substitutions, and alterations are also possible without departing from the spirit and scope of this disclosure, as defined by the following claims.

The invention claimed is:

1. A disposable reamer to create blind holes in a bone, the disposable reamer comprising:
   A) a reamer body connectable to a reamer shaft, the reamer body having a shell curvature comprising at least a portion of a hemisphere, a convex curved exterior surface and a concave curved interior surface, extending from an apex to a lower edge, the reamer body being rotatable about a perpendicular axis;
   B) a first left-hand spiral reamer blade, the first left-hand spiral reamer blade has a first cutting edge fluidly extending from a first inclined blade ramp, the first cutting edge and the first inclined blade ramp extend outwardly from the convex curved exterior surface of the reamer body, the first inclined blade ramp and the first cutting edge extend from the lower edge toward the apex, and a portion of the first cutting edge is positioned over a first left-hand spiral slot, the first left-hand spiral slot (i) extends from the convex curved exterior surface to the concave curved interior surface and (ii) is positioned between the lower edge and the apex while not contacting (a) the lower edge and (b) the apex;
   C) a second left-hand spiral reamer blade, the second left-hand spiral reamer blade has a second cutting edge fluidly extending from a second inclined blade ramp, the second cutting edge and the second inclined blade ramp extend outwardly from the convex curved exterior surface of the reamer body, the second inclined blade ramp and the second cutting edge extend from the lower edge toward the apex so the first cutting edge contacts the second cutting edge at the apex, and a portion of the second cutting edge is positioned over a second left-hand spiral slot, the second left-hand spiral slot (i) extends from the convex curved exterior surface to the concave curved interior surface and (ii) is positioned between the lower edge and the apex while not contacting (a) the lower edge and (b) the apex;
   D) the first left-hand spiral slot has a first length extending from a first proximal end to a first distal end, a first width extending from a first trailing edge to a first leading edge, a first apex distance between the apex on the convex curved exterior surface and the first distal end, and a first edge distance between the first proximal end and the lower edge;
   E) the second left-hand spiral slot has a second length extending from a second proximal end to a second distal end, a second width extending from a second trailing edge to a second leading edge, a second apex distance between the apex on the convex curved exterior surface and the second distal end, and a second edge distance between the second proximal end and the lower edge;
   wherein when the reamer body rotates and contacts a bone or tissue, the first and second cutting edges (a) cut bone or tissue to create cut bone chips or cut tissue chips, and (b) pushes the cut bone chips or the cut tissue chips toward the apex of the convex curved exterior surface, so the cut bone chips or the cut tissue chips break and dislodge free from the bone or the tissue.

2. The reamer of claim 1 further comprising:
   G) a third left-hand spiral reamer blade, the third left-hand spiral reamer blade has a third cutting edge fluidly extending from a third inclined blade ramp, the third cutting edge and the third inclined blade ramp extend outwardly from the convex curved exterior surface of the reamer body, the third inclined blade ramp and the third cutting edge extend from the lower edge toward the apex to form a first debris gap positioned between (a) the third reamer blade and (b) the first and second reamer blades, and a portion of the third cutting edge is positioned over a third left-hand spiral slot, the third left-hand spiral slot (i) extends from the convex curved exterior surface to the concave curved interior surface and (ii) is positioned between the lower edge and the apex while not contacting (a) the lower edge and (b) the apex;
   H) the third left-hand spiral slot has a third length extending from a third proximal end to a third distal end, a third width extending from a third trailing edge to a third leading edge, a third apex distance between the apex on the convex curved exterior surface and the third distal end, and a third edge distance between the third proximal end and the lower edge;
   wherein when the reamer body rotates and contacts a bone or tissue, the first, second, and third, cutting edges (a) cut bone or tissue to create cut bone chips or cut tissue chips, and (b) pushes the cut bone chips or the cut tissue chips toward the apex of the convex curved exterior surface, so the cut bone chips or the cut tissue chips break and dislodge free from the bone or the tissue.

3. The reamer of claim 2 further comprising:
   I) a fourth left-hand spiral reamer blade, the fourth left-hand spiral reamer blade has a fourth cutting edge fluidly extending from a fourth inclined blade ramp, the fourth cutting edge and the fourth inclined blade ramp extend outwardly from the convex curved exterior surface of the reamer body, the fourth inclined blade ramp and the fourth cutting edge extend from the lower edge toward the apex to form a second debris gap positioned between (a) the fourth reamer blade and (b) the first and second reamer blades, and a portion of the fourth cutting edge is positioned over a fourth left-hand spiral slot, the fourth left-hand spiral slot (i) extends from the convex curved exterior surface to the concave curved interior surface and (ii) is positioned between the lower edge and the apex while not contacting (a) the lower edge and (b) the apex;

J) the fourth left-hand spiral slot has a fourth length extending from a fourth proximal end to a fourth distal end, a fourth width extending from a fourth trailing edge to a fourth leading edge, a fourth apex distance between the apex on the convex curved exterior surface and the fourth distal end, and a fourth edge distance between the fourth proximal end and the lower edge;

wherein when the reamer body rotates and contacts a bone or tissue, the first, second, third, and fourth cutting edges (a) cut bone or tissue to create cut bone chips or cut tissue chips, and (b) pushes the cut bone chips or the cut tissue chips toward the apex of the convex curved exterior surface, so the cut bone chips or the cut tissue chips break and dislodge free from the bone or the tissue.

4. The reamer of claim 3 wherein the first apex distance, the second apex distance, the third apex distance, and the fourth apex distance are the same; and the first edge distance, the second edge distance, the third edge distance, and the fourth edge distance are the same.

5. The reamer of claim 1 wherein an angle of the first inclined blade ramp and the second inclined blade ramp ranges from 1° to 30°; and the lower edge of the reamer body resides along an imaginary equatorial plane.

6. The reamer of claim 5 wherein the reamer shaft has a distal end extending downward along the perpendicular axis from the apex of the concave curved interior surface (a) toward the imaginary equatorial plane, (b) toward the imaginary equatorial plane and the reamer shaft has a proximal end, the proximal end terminating at the imaginary equatorial plane, or (c) toward the imaginary equatorial plane and the reamer shaft has a proximal end, the proximal end extending beyond the imaginary equatorial plane.

7. The reamer of claim 5 wherein the reamer shaft has a proximal end, and the reamer shaft has at least one interconnection rod extending from or near the proximal end, and the at least one interconnection rod (a) is parallel to or in the same plane as the imaginary equatorial plane, (b) extends toward the concave curved interior surface; and (c) does not contact the concave curved interior surface.

8. The reamer of claim 1 wherein the second apex distance and the first apex distance are the same; and the second edge distance and the first edge distance are the same.

9. The reamer of claim 1 wherein the reamer body and the first left-hand spiral reamer blade are made of the same material selected from the group consisting of stainless steel, cobalt chrome, titanium, carbon fiber reinforced plastic, binder material from a three-dimensional metal binder jetting printing process, and combinations thereof.

10. The reamer of claim 1 wherein the reamer body is manufactured by a three-dimensional metal binder jetting printing process.

11. The reamer of claim 1 wherein the apex of the concave curved interior surface of the reamer body has a socket or a male adapter, and the reamer shaft is connectable to the socket or the male adapter.

12. A disposable reamer to create blind holes in a bone, the disposable reamer comprising:
A) a reamer body connectable to a reamer shaft, the reamer body having a shell curvature comprising at least a portion of a hemisphere, a convex curved exterior surface and a concave curved interior surface, extending from an apex to a lower edge, the reamer body being rotatable about a perpendicular axis;
B) a first left-hand spiral reamer blade, the first left-hand spiral reamer blade has a first cutting edge fluidly extending from a first inclined blade ramp, the first cutting edge and the first inclined blade ramp extend outwardly from the convex curved exterior surface of the reamer body, the first inclined blade ramp and the first cutting edge extend from the lower edge toward the apex, and the first cutting edge is never positioned over a first left-hand spiral slot, the first left-hand spiral slot (i) extends from the convex curved exterior surface to the concave curved interior surface and (ii) is positioned between the lower edge and the apex while not contacting (a) the lower edge and (b) the apex;
C) a second left-hand spiral reamer blade, the second left-hand spiral reamer blade has a second cutting edge fluidly extending from a second inclined blade ramp, the second cutting edge and the second inclined blade ramp extend outwardly from the convex curved exterior surface of the reamer body, the second inclined blade ramp and the second cutting edge extend from the lower edge toward the apex so the first cutting edge contacts the second cutting edge at the apex, and the second cutting edge is never positioned over a second left-hand spiral slot, the second left-hand spiral slot (i) extends from the convex curved exterior surface to the concave curved interior surface and (ii) is positioned between the lower edge and the apex while not contacting (a) the lower edge and (b) the apex;
D) the first left-hand spiral slot has a first length extending from a first proximal end to a first distal end, a first width extending from a first trailing edge to a first leading edge, a first apex distance between the apex on the convex curved exterior surface and the first distal end, and a first edge distance between the first proximal end and the lower edge;
E) the second left-hand spiral slot has a second length extending from a second proximal end to a second distal end, a second width extending from a second trailing edge to a second leading edge, a second apex distance between the apex on the convex curved exterior surface and the second distal end, and a second edge distance between the second proximal end and the lower edge;
wherein when the reamer body rotates and contacts a bone or tissue, the first and second cutting edges (a) cut bone or tissue to create cut bone chips or cut tissue chips, and (b) pushes the cut bone chips or the cut tissue chips toward the apex of the convex curved exterior surface, so the cut bone chips or the cut tissue chips break and dislodge free from the bone or the tissue.

13. The reamer of claim 12 further comprising:
G) a third left-hand spiral reamer blade, the third left-hand spiral reamer blade has a third cutting edge fluidly extending from a third inclined blade ramp, the third cutting edge and the third inclined blade ramp extend outwardly from the convex curved exterior surface of the reamer body, the third inclined blade ramp and the third cutting edge extend from the lower edge toward the apex to form a first debris gap positioned between (a) the third reamer blade and (b) the first and second reamer blades, and the third cutting edge is never positioned over a third left-hand spiral slot, the third left-hand spiral slot (i) extends from the convex curved exterior surface to the concave curved interior surface and (ii) is positioned between the lower edge and the apex while not contacting (a) the lower edge and (b) the apex;

H) a fourth left-hand spiral reamer blade, the fourth left-hand spiral reamer blade has a fourth cutting edge fluidly extending from a fourth inclined blade ramp, the fourth cutting edge and the fourth inclined blade ramp extend outwardly from the convex curved exterior surface of the reamer body, the fourth inclined blade ramp and the fourth cutting edge extend from the lower edge toward the apex to form a second debris gap positioned between (a) the fourth reamer blade and (b) the first and second reamer blades, and the fourth cutting edge is never positioned over a fourth left-hand spiral slot, the fourth left-hand spiral slot (i) extends from the convex curved exterior surface to the concave curved interior surface and (ii) is positioned between the lower edge and the apex while not contacting (a) the lower edge and (b) the apex;

I) the third left-hand spiral slot has a third length extending from a third proximal end to a third distal end, a third width extending from a third trailing edge to a third leading edge, a third apex distance between the apex on the convex curved exterior surface and the third distal end, and a third edge distance between the third proximal end and the lower edge;

J) the fourth left-hand spiral slot has a fourth length extending from a fourth proximal end to a fourth distal end, a fourth width extending from a fourth trailing edge to a fourth leading edge, a fourth apex distance between the apex on the convex curved exterior surface and the fourth distal end, and a fourth edge distance between the fourth proximal end and the lower edge;

wherein when the reamer body rotates and contacts a bone or tissue, the first, second, third, and fourth cutting edges (a) cut bone or tissue to create cut bone chips or cut tissue chips, and (b) pushes the cut bone chips or the cut tissue chips toward the apex of the convex curved exterior surface, so the cut bone chips or the cut tissue chips break and dislodge free from the bone or the tissue.

14. The reamer of claim 13 wherein the reamer body, first left-hand spiral reamer blade, second left-hand spiral reamer blade, third left-hand spiral reamer blade, and fourth left-hand spiral reamer blade are made of the same material selected from the group consisting of stainless steel, cobalt chrome, titanium, carbon fiber reinforced plastic, binder material from a three-dimensional metal binder jetting printing process, and combinations thereof.

15. The reamer of claim 12 wherein an angle of the first inclined blade ramp and the second inclined blade ramp ranges from 1° to 30° and the lower edge of the reamer body resides along an imaginary equatorial plane.

16. The reamer of claim 15 wherein the reamer shaft has a distal end extending downward along the perpendicular axis from the apex of the concave curved interior surface (a) toward the imaginary equatorial plane, (b) toward the imaginary equatorial plane and the reamer shaft has a proximal end, the proximal end terminating at the imaginary equatorial plane, or (c) toward the imaginary equatorial plane and the reamer shaft has a proximal end, the proximal end extending beyond the imaginary equatorial plane.

17. The reamer of claim 15 wherein the reamer shaft has a proximal end, and the reamer shaft has at least one interconnection rod extending from or near the proximal end, and the at least one interconnection rod (a) is parallel to or in the same plane as the imaginary equatorial plane, (b) extends toward the concave curved interior surface; and (c) does not contact the concave curved interior surface.

18. The reamer of claim 12 wherein the second apex distance and the first apex distance are the same; and the second edge distance and the first edge distance are the same.

19. The reamer of claim 12 wherein the reamer body is manufactured by a three-dimensional metal binder jetting printing process.

* * * * *